United States Patent [19]
Oberhardt

[11] Patent Number: 5,601,991
[45] Date of Patent: Feb. 11, 1997

[54] DRY CHEMISTRY CASCADE IMMUNOASSAY AND AFFINITY ASSAY

[75] Inventor: Bruce J. Oberhardt, Raleigh, N.C.

[73] Assignee: Cardiovascular Diagnostics, Inc., Durham, N.C.

[21] Appl. No.: 387,373

[22] Filed: Feb. 13, 1995

Related U.S. Application Data

[63] Continuation of Ser. No. 18,415, Feb. 17, 1993, abandoned.

[51] Int. Cl.$^6$ .................................................. G01N 33/53
[52] U.S. Cl. ............................. 435/7.91; 435/5; 435/6; 435/7.2; 435/7.4; 435/7.7; 435/7.92; 435/7.93; 435/7.94; 435/13; 435/808; 435/810; 435/970; 436/526; 436/527; 436/46; 436/805; 436/806; 436/807; 436/808; 436/809; 422/57; 422/58; 422/61; 422/73
[58] Field of Search ............................ 435/5, 6, 7.2, 7.4, 435/7.7, 7.8, 7.91, 7.92, 7.93, 7.94, 7.95, 13, 805, 808, 810, 970, 975; 436/526, 527, 46, 69, 805, 806, 807, 808, 809, 810; 422/57, 58, 61, 73; 73/64.43, 863.61, 863.71; 209/212, 213, 214, 215; 210/695, 222

[56] References Cited

U.S. PATENT DOCUMENTS

| | | | |
|---|---|---|---|
| 4,668,621 | 5/1987 | Doellgast | 435/13 |
| 4,849,340 | 7/1989 | Oberhardt | 435/13 |
| 4,960,693 | 10/1990 | Siddiqi et al. | 435/15 X |
| 4,985,354 | 1/1991 | Toyomaki et al. | 435/13 |
| 5,093,237 | 3/1992 | Enomoto | 435/13 |
| 5,110,727 | 5/1992 | Oberhardt | 435/13 |

FOREIGN PATENT DOCUMENTS

| | | |
|---|---|---|
| 0123265A1 | 10/1984 | European Pat. Off. |
| 0241140 | 10/1987 | European Pat. Off. |

OTHER PUBLICATIONS

Enzyme–Linked Coagulation Assay: V. Amplified Blotting Assays Using Snake Venom Conjugates, Kristine H. Durkee, et al., Analytical Biochemistry, 184, 375–380 (1990).
Enzyme–Immunassay: A Review ), M. Oellerich, J. Clin. Chem. Clin. Biochem., vol. 22, No. 12, pp. 895–904.
Immunoassay, Dan Monroe, Analytical Chemistry, vol. 56, No. 8, Jul. 1984.
Zymogen Activation: A New System for Homogeneous Ligand–Binding Assay, Diane A. Blake, et al. Clin. Chem. 30/9, 1452–1456 (1984).
Enzyme–Linked Coagulation Assay, IV. Sensitive Sandwich Enzyme–Linked Immunoabsorbent Assays Using Russell's Viper Venom Factor X Activator–Antibody Conjugates, George J. Doellgast, Analytical Biochemistry 167, 97–105 (1987).

(List continued on next page.)

*Primary Examiner*—Paula K. Hutzell
*Assistant Examiner*—Susan C. Wolski
*Attorney, Agent, or Firm*—Oblon, Spivak, McClelland, Maier & Neustadt, P.C.

[57] ABSTRACT

A method is described for performing an affinity assay comprising contacting a sample to be assayed for the presence of an analyte with a dry reagent containing the analyte (hapten, antigen, antibody, receptor, or complementary polynucleotide) bound to a reaction cascade initiator, an antibody or other binding pair partner reactive with said analyte, and magnetic particles, to form an assay mixture in a reaction chamber, incubating the assay mixture, applying an oscillating or moving static magnetic field to the assay mixture, activating the reaction cascade initiator to initiate a reaction cascade, monitoring the response of the magnetic particles to the oscillating or moving static magnetic field to provide a time varying signal, and determining the analyte concentration of the sample by analysis of the time varying signal, as well as a kit for performing the assay and a diagnostic system for performing the assay.

86 Claims, 10 Drawing Sheets

OTHER PUBLICATIONS

Enzyme–Linked Coagulation Assay, III. Sensitive Immunoassays for Clotting Factors II, VII, and X, George J. Doellgast, Analytical Biochemistry, 162, 102–114 (1987).

Enzyme Linked Coagulation Assay II. A Sensitive Assay for Tissue Factor and Factors II, VII, and X, George J. Doellgast, et al., Analytical Chemistry, 152, 199–207 (1986).

Enzyme–Linked Coagulation Assay: A Clot–Based Solid–Phase Assay for Thrombin, George J. Doellgast, et al., Analytical Biochemistry, 147, 529–534 (1985).

Extrinsic–Pathway Enzyme–Linked Coagulation Assay (EP–ELCA). A Clot–Based Alternative to Prothrombin Time for Measurment of Extinsic Pathway Factors in Plasma, George J. Doellgast, et al. Clinical Chemistry, vol. 34, No. 2, 294–299 (1988).

Photolysis and Deacylation of Inhibited Chymotrypsin, Barry L. Stoddard, et al., Biochemistry, 1990, 29., p. 8042.

Structure and Activity of Two Photoreversible Cinnamates Bound to Chymotrypsin, Barry L. Stoddard, et al., Biochemistry, 1990, 29., p. 4871.

Acyl Thrombin Photochemistry: Kinetics for Deacylation of Enzyme Cinnamate Geometric Isomers, Ned A. Porter, et al., Journal of the American Chemical Society, 1989, 111, 7616.

Kinetic and Thermodynamic Properties of Wild–Type and Engineered Mutants of Tyrosyl–tRNA Synthetase Analyzed by Pyrophosphate–Exchange Kinetics, Tim. N. C. Wells, et al., Biochemistry 1991, 5151–5156.

Enzyme Linked Fibrinolytic Assay (ELFA). A New Method for the Measurement of t–PA in Plasma Using Enzyme Labeled Fibrin, Mark X. Triscott, et al., Thrombosis Research 59; 723–733, 1990.

Proclotting Enzyme from Horseshoe Crab Hemocytes, DNA Cloning, Disulfide Locations, and Subcellular Localization, Tatsuchi Muta, et al., The Journal of Biological Chemistry, vol. 265, No. 36, Issue of Dec. 25, pp. 22426–22433, 1990.

Stability of Gels Formed Following Coagulation of Limulus Amebocyte Lysate: Lack of Covalent Crosslinking of Coagulin, Robert I. Roth, et al., Thrombosis Research 55; 25–36, 1989.

A New Endotoxin Sensitive Factor Associated with Hemolymph Coagulation System of Horseshoe Crab (Limulidae), Makoto Ohki, et al., Febs Letters, vol. 120, No. 2, Nov. 1980.

The Proteolytic Activiation Systems of Complement, Kenneth B. M. Reid, et al., Ann.Rev.Biochem., 1981, 50:433–64.

Portable Simultaneous Multiple Analyte Whole–Blood Analyzer for Point–of–Care Testing, Carl T. Schembri, et al., Clinical Chemistry, vol. 38, No. 9, pp. 1665–1670, 1992.

Dry Reagent Technology for Rapid, Convenient Measurements of Blood Coagulation and Fibrinolysis, Bruce J. Oberhardt, et al., Clinical Chemistry, 37, 520 (1991).

Photocoagulation of Human Plasma: Acyl Serine Proteinase Photochemistry, Ned A. Porter, et al. Photochemistry and Photobiology, vol. 51, No. 1, pp. 37–43, 1990.

Enzyme–Immunoassay, G. Brian Wisdom, Clin. Chem. vol. 22, No. 8, 1243–1255 (1976).

DRY CHEMISTRY CASCADE IMMUNOASSAY AND AFFINITY ASSAY

This application is a continuation of application Ser. No. 08/018,415, filed Feb. 17, 1993, now abandoned.

BACKGROUND OF THE INVENTION

1. Field of the Invention

The present invention relates to a method for performing binding pair assays, including immunoassays, in a dry chemistry format.

2. Discussion of the Background

There are a variety of binding pair assays. These include immunoassays of various types, DNA and RNA probe assays, and a variety of other ligand-receptor assays of biological importance. Immunoassays are available today to provide quantitative measurement of a particular antigen or antibody that may be of interest. Among these types of assays are the enzyme-immunoassays (see review articles by Oellerich, J. Clin. Chem. Clin. Biochem. Vol. 22, 1984, pp. 895–904; Monroe, Analytical Chemistry, Vol. 56, No. 8, 1984, pp. 921a–931a; and Wisdom, Clin. Chem. 22/8, 1976, 1243–1255). In enzyme-immunoassays, the enzyme is used as a label or marker which is bound to one member of the antigen-antibody pair identical to that in the sample to be measured. The enzyme bound antigen/antibody then competes with the sample antigen/antibody for the binding site on a limited supply of its complement antibody/antigen.

Binding pair assays must be somehow coupled to a transducer or measurement system to produce a measurement or result. All assays of this type are coupled to another system to provide the measurement. In the above example of the enzyme immunoassay, the level of the sample antigen/antibody is then measured indirectly by measurement of the enzyme activity using a variety of methods such as colorimetry, chemiluminescence, fluorimetry, or bioluminescence.

The problem with conventional immunoassays, and more generally with conventional binding pair assays, is that these systems suffer from three distinct disadvantages:

1) They cannot provide quantitative whole blood measurements. Because the quality of an enzyme-immunoassay depends very much on the purity of the antigen or hapten to be measured, they are especially not useful in analyzing whole blood samples. In addition, whole blood creates optical interferences with photometric measurements and minimizes the potential to extract useful signals from the system.

2) They suffer from long turnaround times. The reactions are slow and tests take a long time to provide results.

3) They involve multiple steps. They are labor intensive if manually performed or require expensive, complicated instrumentation to automate the many incubation, washing, sample, and reagent addition steps.

It has been shown that the magnetic particle interrogation method allows convenient dry chemistry kinetic measurements on blood coagulation to be made on whole blood samples (see Oberhardt, U.S. Pat. Nos. 4,849,340 and 5,110,727). In the magnetic particle interrogation method, a measured amount of a blood sample is added to a reaction slide that contains a combination of magnetic particles and at least one dry reagent. Upon reaction between the sample and the dry reagent and application of a moving or oscillating magnetic field, the movement of the magnetic particles is monitored to detect the clotting endpoint and thus obtain clotting times. This is significant, in that there are very few methodologies capable of achieving convenient, quantitative measurements in whole blood and other difficult biological samples.

However, in order to use this same technology for immunoassays and, more generally, binding pair assays of different types, a way must be found to couple the existing assay system with an immunologic or binding pair "front end".

One possible solution would be to bind the antibodies or antigens directly to the magnetic particles. However, while binding antibodies or antigens to the magnetic particles provides a system that can read immunological reactions, such a system is simultaneously very difficult to use in a reproducible, dry chemistry format because of the nature of all particles to aggregate and thereby minimize their thermodynamic free energy, resulting in a stable but aggregated system. For example, magnetic latex is difficult to quantify with magnetic interrogation. When used with surface antigen or antibody molecules, these particles have provided poor reproducibility. The use of other types of magnetic particles with surface bound immunological molecules has not been entirely successful. The use of magnetite ($Fe_3O_4$) particles in a "passive" mode has also been considered; that is, without surface antibody or antigen, but development of a workable assay system based on the passive particle approach has met with little success.

While the passive particle approach is elegant in concept, it is unclear how an immunological or binding pair "front end" can be coupled to the magnetic particle interrogation technology that has only been used previously for measurement of coagulation or fibrinolysis assays.

Enzyme-linked coagulation assays have been proposed that utilize enzymes bound to antibodies or antigens, wherein the enzymes used are active factors in the coagulation cascade reaction system (see Doellgast et al. Analytical Biochemistry, 147, (1985) 529–534; 152, (1986) 199–207; 162, (1987) 102–114; 167, (1987) 97–105; and 184, (1990) 375–380; Clin. Chem. 34/2, (1988) 294–299; see also Doellgast, U.S. Pat. No. 4,668,621). However in each of the systems proposed, there are required one or more separation, washing, and dilution steps, or long sample turnaround times.

Doellgast et al. have also proposed an enzyme-linked fibrinolytic assay to measure the activity of plasminogen activators (e.g., t-PA) (Thrombosis Research, 59, (1990) 723–733). However, as in the case of the coagulation assays above, multiple separation, washing, and dilution steps are required to perform the assay. Blake et al. have proposed an immunoassay based on the coagulation cascade or other cascade systems (Clin. Chem. (1984) 30/9 1452–14156). This system utilizes steric hindrance and not separation and washing steps. However, the system is based on colorimetry and therefore is unsuitable for analysis of whole blood samples or diluted blood samples. There are currently no examples of similar attempts with DNA/RNA probes or other binding pair assays.

It is therefore highly desirable to provide a rapid, sensitive, convenient binding pair assay system for use in whole blood samples that is quantitative and easy to use.

SUMMARY OF THE INVENTION

Accordingly, one object of the present invention is to provide a rapid, sensitive, convenient binding pair assay system for use in biologically difficult samples that is quantitative and easy to use.

Another object of the present invention is to provide a binding pair assay system for use in biologically difficult samples that utilizes an initiator bound to one member of the binding pair that upon activation initiates a reaction cascade that allows for the measurement of the binding pair member of interest without requiring separation or washing steps.

Another object of the present invention is to provide a binding pair assay system as described above in which the initiator is an enzyme in the blood coagulation cascade or the lytic cascade.

Another object of the present invention is to provide an immunoassay system that is useful in whole blood systems.

Another object of the present invention is to provide assays for small molecules, such as therapeutic drugs used to treat cardiovascular disease, for example digoxin, quinidine, lidocaine, mexiletine, sotalol, imipramine, propafenone, cibenzoline, encainide, flecainide, indecainide, moricizine, pentisamide, tocainide, betaxolol, bisoprolol, penbutolol, amiodarone, bethanidine, meobentine, bepridil, diltiazem and other antiarrhythmic drugs, that utilize a blood coagulation cascade for amplification and a magnetic particle interrogation method for detection of the coagulation endpoint.

Another object of the present invention is to provide rapid and convenient immunoassays for large molecules, such as apolipoprotein A-1, apolipoprotein B-100, apolipoprotein E, lipoprotein Lp(a), immunoglobulins such as IgM, fibrinogen, and others, that utilize a blood coagulation cascade for amplification and a magnetic particle interrogation method for detection of the coagulation endpoint.

Another object of the present invention is to provide immunoassays for important cardiovascular proteins, such as: CK-MB, myoglobin, fibrinogen, plasminogen, troponin, PAI-1, thrombomodulin, and thrombin-antithrombin complex, that utilize a blood coagulation cascade for amplification and a magnetic particle interrogation method for detection of the coagulation endpoint.

Another object of the present invention is to provide a convenient assay for cellular elements or their surface antigenic or receptor molecules, such as blood platelets or specific receptors, i.e., IIb IIIa, etc.; red blood cells or specific antigens, i.e., Rho; white blood cells, or specific antigens, i.e., histocompatibility antigens; or bacterial cells, viruses, rickettsia, molds, or yeasts, that utilizes a blood coagulation cascade for amplification and a magnetic particle interrogation method for detection of the coagulation endpoint.

Another object of the present invention is to provide rapid, convenient quantitative immunoassays for important healthcare screening and disease management applications, such as HIV antigen, CD4/CD8 and PAN T in acquired immune deficiency syndrome (AIDS) and prostate specific antigen (PSA) in prostate cancer, that utilize a blood coagulation cascade for amplification and a magnetic particles interrogation method for detection of the coagulation endpoint.

Another object of the present invention is to provide rapid and convenient diagnostic immunoassays for hormones, such as insulin, T4, T3, ACTH, hCG, TSH, Angiotensin II, and others, that utilize a blood coagulation cascade for amplification and a magnetic particle interrogation method for detection of the coagulation endpoint.

Another object of the present invention is to provide rapid and convenient diagnostic immunoassays for signal or structural elements outside or within cells, such as collagen, adhesion receptors such as fibronectin, vitronectin, other integrins, glycosaminoglycans, proteoglycans, annexins, cytoskeletal components, cytokines, growth factors, and others, that utilize a blood coagulation cascade for amplification and a magnetic particle interrogation method for detection of the coagulation endpoint.

Another object of the present invention is to provide rapid and convenient diagnostic tests for specific polynucleotides, such as those found in genetic material in cells and viruses, that utilize a blood coagulation cascade for amplification and a magnetic particle interrogation method for detection of the coagulation endpoint.

Another object of the present invention is to provide convenient, rapid diagnostic tests for difficult biological samples, other than blood, such as lung lavage or saliva, that utilize a blood coagulation cascade for amplification and a magnetic particle interrogation method for detection of the coagulation endpoint.

Another object of the present invention is to provide an assay for blood or other difficult biological samples based on possible cascade systems, other than human blood coagulation, such as: the bovine blood coagulation cascade, bovine milk coagulation cascade, human or bovine fibrinolytic cascades, porcine cascades, insect blood coagulation cascades or horseshoe crab hemolymph cascade, that utilizes the cascade for amplification and a magnetic particle interrogation method for detection of the coagulation endpoint.

Another object of the present invention is to provide rapid and convenient quantitative diagnostic assays for ligands or receptors, such as: von Willebrand factor and its collagen receptor and platelet GPIb receptor, thrombin and thrombomodulin, acetylcholine and its receptors, and others, that utilize a blood coagulation cascade for amplification and a magnetic particle interrogation method for detection of the coagulation endpoint.

Another object of the present invention is to provide a panel of affinity assays, e.g., immunoassays for different but related analytes, to facilitate medical diagnostic decision making from a single application of sample to a reaction slide sample well connected in parallel to multiple reaction volumes where individual assays are performed, that utilizes a coagulation cascade for amplification and a magnetic particle interrogation method for detection of the coagulation endpoint.

Another object of the present invention is to provide a convenient and effective system for performing dry chemistry quantitative affinity assays comprising a reaction slide and an apparatus utilizing rotating magnetic fields and optical detection and illumination means.

These and other objects have been satisfied by the discovery of a method for performing an affinity assay comprising contacting a sample to be assayed for the presence of an analyte with a dry reagent containing the analyte (small or large molecule, such as a hapten, protein, antibody, receptor, or complementary polynucleotide) bound to a reaction cascade initiator, an antibody reactive with said analyte, and magnetic particles, to form an assay mixture in a reaction chamber, incubating the assay mixture, applying an oscillating or moving static magnetic field to the assay mixture, activating the reaction cascade initiator to initiate a reaction cascade, monitoring the response of the magnetic particles to the oscillating or rotating magnetic field to provide a time varying signal, and determining the analyte concentration of the sample by analysis of the time varying signal.

BRIEF DESCRIPTION OF THE FIGURES

A more complete appreciation of the invention and many of the attendant advantages thereof will be readily obtained as the same become better understood by reference to the following detailed description when considered in connection with the accompanying figures, wherein:

FIGS. 11a, 11b, and 11c show how individual reaction slides that are filled with reagent, processed, and dried independently can be combined on a common carrier and filled with sample from a common sample well to provide an assay panel.

DETAILED DISCUSSION OF THE PREFERRED EMBODIMENTS

The present invention provides a method for performing an affinity assay comprising:

contacting a sample to be assayed for the presence of an analyte with a dry reagent comprising the analyte covalently bound to a reaction cascade initiator, an antibody reactive with the analyte, and magnetic particles, to form an assay mixture in a reaction chamber;

incubating the assay mixture;

applying a magnetic field to the assay mixture;

activating the reaction cascade initiator to initiate a reaction cascade;

monitoring a response of the magnetic particles by optical means to provide an optical oscillation signal; and determining the analyte concentration in the sample by analysis of the optical oscillation signal.

The method of the present invention can be used for a wide variety of binding pair assays, including immunoassays. A few examples of the types of assays that could be performed using the method of the present invention include immunoassays for soluble antigens, cellular immunoassays, receptor-ligand assays of various types that are non-immunological, and DNA and RNA probes.

Figure 1:
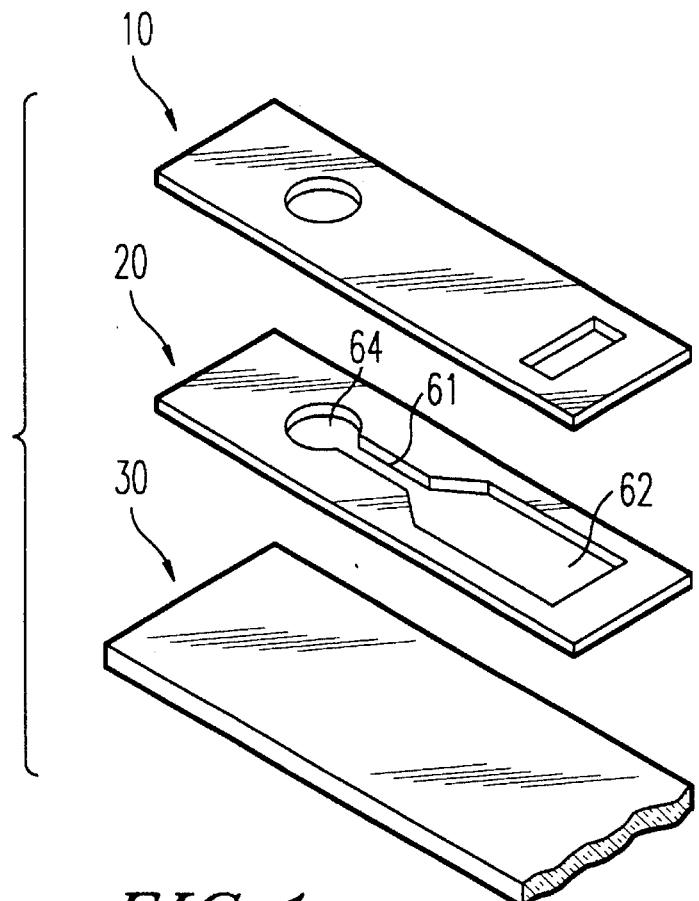
FIG. 1 is an exploded view of a reaction slide useful with the present invention (described in U.S. Pat. Nos. 4,849,340 and 5,110,727 which are both hereby incorporated by reference) showing a base support (30), a reaction plate or spacer (20) and a reaction cover (10), and the positions of the sample well (64), passageway (61), and reaction chamber (62), with passageway (61) and reaction chamber (62) comprising the reaction volume.
Figure 2:
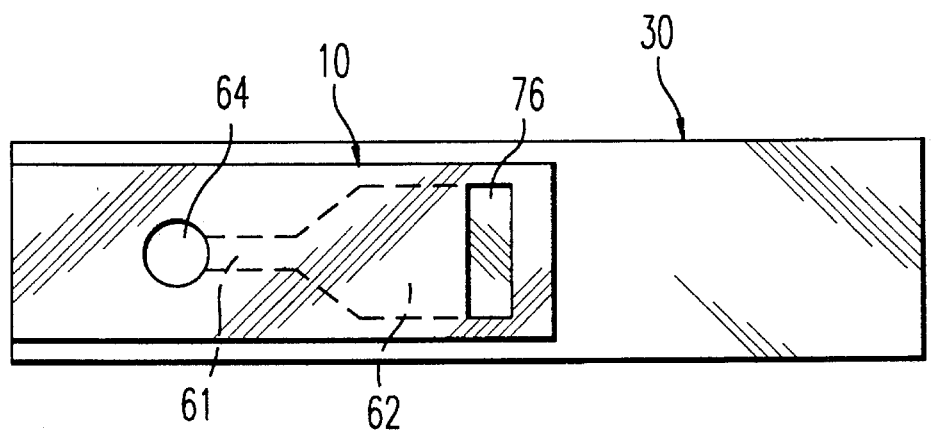
FIG. 2 is a top view of the assembled reaction slide.

In a particularly preferred embodiment, the present method is performed on a reaction slide, one example of which is depicted in FIG. 1 and FIG. 2. The reaction slide comprises a support member (30) to which is attached a reaction plate or spacer (20). A reaction chamber (62) is defined in the reaction plate (20) by removal of a portion of the material in the center of the reaction plate. If material is removed or "punched out" across the minor dimension or thickness of the reaction plate, a third structural element or cover (10) is utilized to form the ceiling of the reaction chamber. Two, three or more structural elements comprising the reaction slide may be bonded together in various ways, (as discussed for example in Oberhardt, U.S. Pat. Nos. 4,849,340 and 5,110,727). Into the reaction chamber (62) is placed the dry reagent material, containing the magnetic particles, initiator-bound analyte, and the antibody reactive with the analyte. All that is required to perform the assay is to place the test card in the testing instrument, to add a drop (or pipette a small amount) of sample to the sample well (64), and allow the sample to transit passageway (61) to fill the reaction chamber (62), thus allowing reaction to occur and reading the result after the reaction is completed.

A suitable sample slide is described in U.S. Pat. No. 5,110,727 by Oberhardt, which contains a description and preparation of such a slide and is hereby incorporated by reference.

Figure 3:
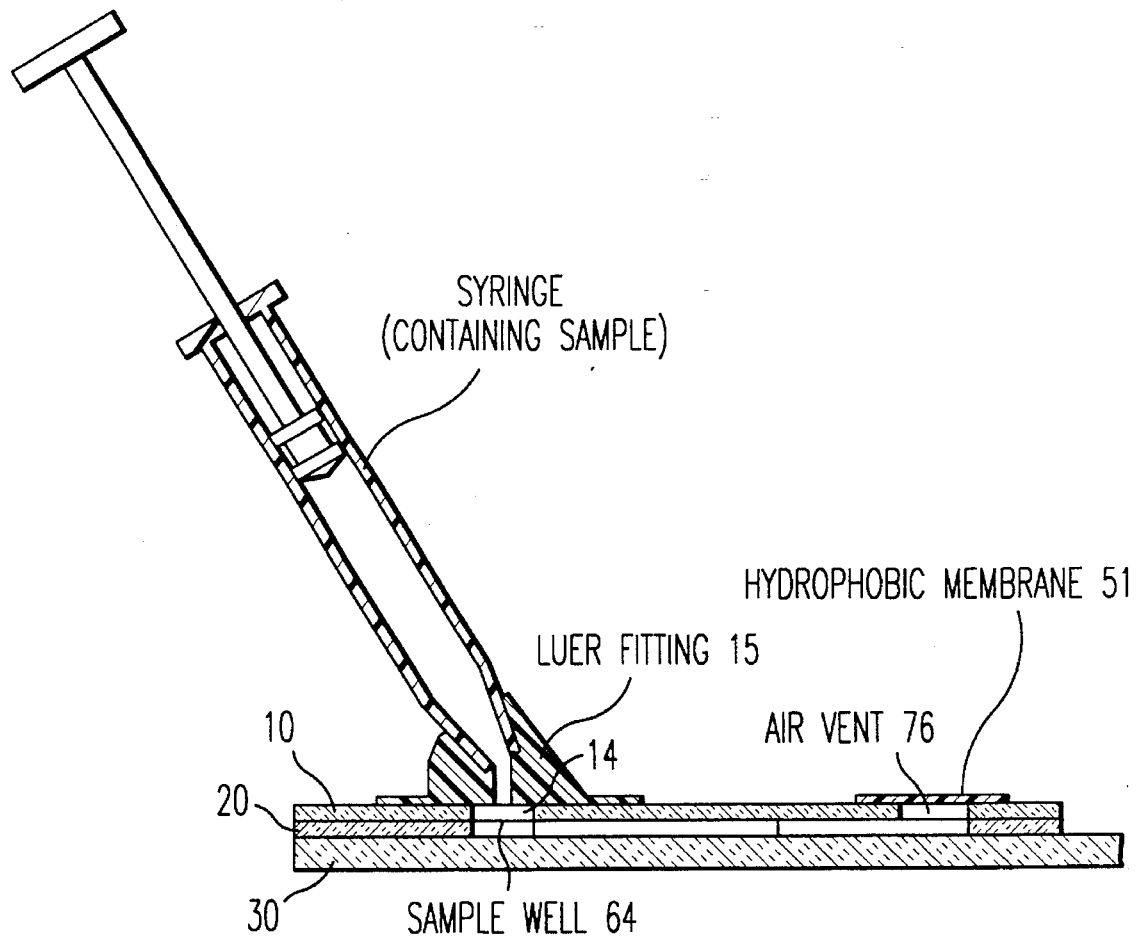
FIG. 3 shows the attachment of a Luer-type adapter (15) to the sample inlet (14) above the sample well (64).

The sample to be analyzed may be added to the reaction slide by any means that allows placement of the sample directly into the sample well or reaction chamber. Suitable means include micropipette, pipette, luer-tipped syringe, and capillary tube. The preferred means are pipette and luer-tipped syringe. The use of a luer-tipped syringe requires that the reaction slide be modified by the addition of a luer adapter (15) at the inlet (14) to the sample well (64) as shown in FIG. 3.

The dry reagent material typically contains the initiator-bound analyte, an antibody reactive with the analyte, and magnetic particles. Depending on the particular assay being performed and the particular reaction cascade, other components, such as enzymes, substrates, activators, neutralizers, and buffers, may be present.

Upon addition of the sample to sample well (64) of the reaction slide, the sample is allowed to transit passageway (61) into reaction chamber (62) to begin reaction with the dry reagent. In a preferred embodiment, the motive force for transferring the sample from sample well (64) to reaction chamber (62) is capillary action caused by passageway (61) and reaction chamber (62) having capillary dimensions, as disclosed in Oberhardt, U.S. Pat. No. 5,110,727.

Figure 4A:
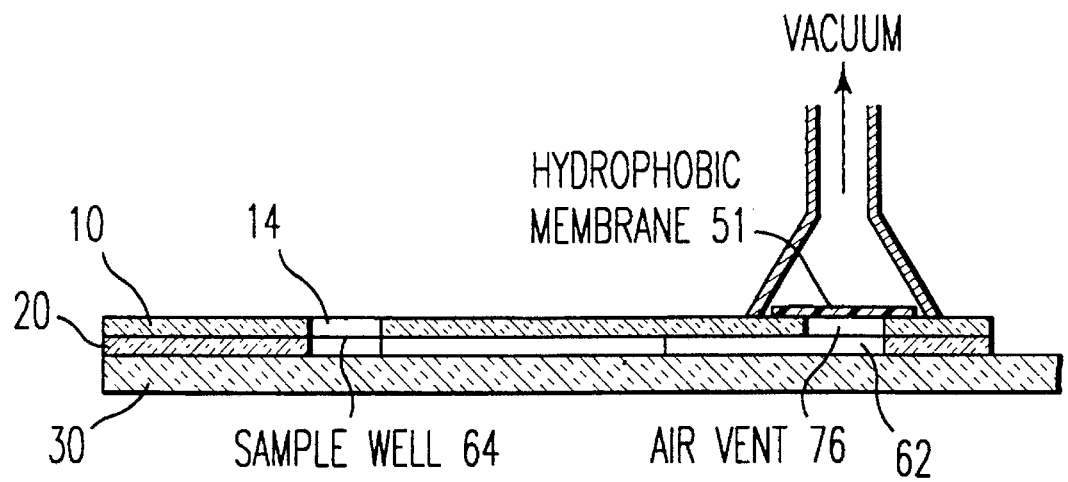
FIGS. 4a and 4b show two alternative methods for introducing the sample into the sample well (64), through the passageway (61), and into the reaction chamber (62): a) via pressure on the sample inlet (14); b) via vacuum on the vent (76).
Figure 4B:
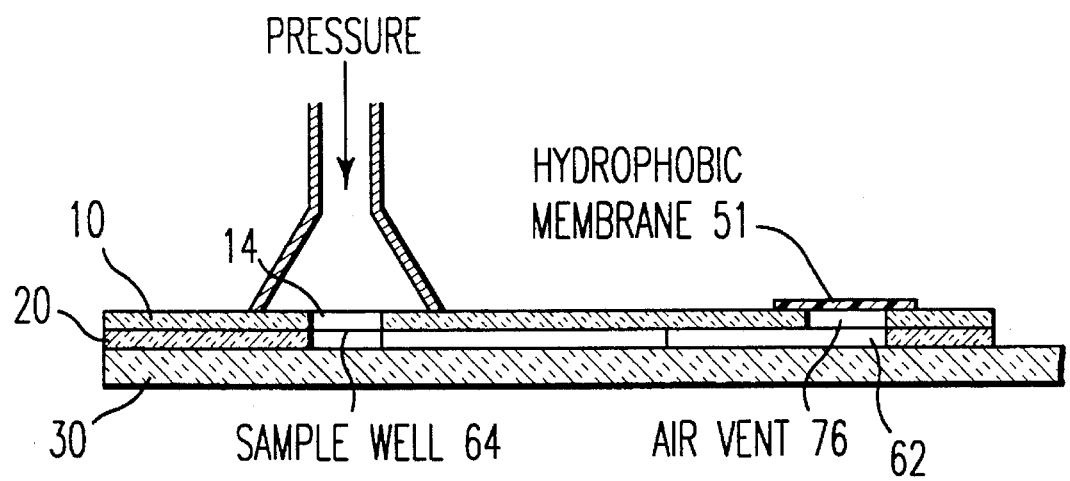

In an alternative embodiment, the motive force for moving the sample is the application of a vacuum source at vent (76) of reaction chamber (62) (see FIG. 4a) or the application of pressure at inlet (14) to the sample well (64) (see FIG. 4b). The level of vacuum or pressure required is a sufficient negative or positive deviation from atmospheric pressure, respectively, to cause movement of the sample from the sample well to the reaction chamber, preferably 5–10 mm less than or greater than atmospheric pressure.

In order to use the vacuum or pressure methods, it is preferred that a hydrophobic membrane (51) be installed over vent (76) of reaction chamber (62) as shown in FIGS. 3, 4a and 4b. The hydrophobic membrane must be gas permeable but liquid impermeable. Preferable membranes are those of 0.5 to 3 mil thickness, having 35–55% porosity with a pore size of from 0.02 to 0.06 micron, most preferably of 1 mil thickness, 45% porosity and a pore size of 0.04 micron. An example of such a membrane is the membrane called CELGARD 2500, available from Hoechst Celanese Corp. In addition, the conduit leading from the sample well to the reaction chamber must be nonwetting or minimally wetting, such that it does not automatically provide capillary action to transport the liquid. This appropriate degree of wetting may be achieved by selection of plastic materials or use of coatings with resultant high contact angles at the liquid/solid interface.

A cascade system biochemistry is the basis for the "back end" of the present assay system. A cascade is a series of reactions, in which the product of the first reaction catalyzes the formation of product in the second reaction, and so on. A cascade system may have as few as two enzymatic steps. Some examples of cascade systems that may be used in the method of the present invention are: the conversion of zymogens to active forms of the enzyme in the human or mammalian blood coagulation cascade; the analogous biochemical cascade in the hemolymph of the horseshoe crab; and insect blood coagulation cascades. An additional cascade system that may be used in the present method is a lytic cascade, such as the human plasmogen activator/plasminogen system. Generally, as one begins higher on the cascade system, the amount of amplification seen in the assay measurement increases. The greater the amplification of the cascade system, the greater the sensitivity of the binding pair assay. However, even at the level of Factor X in the human blood coagulation cascade, the present invention provides sensitivity down to as low as 0.1 picomole of $X_a$ per liter for a 2-step cascade. Thus, enough sensitivity would be present to perform nearly all commercially important immunoassays. For a 3-step cascade the sensitivity may be increased to the femtomole per liter level. For a reaction chamber accepting 25 microliters of sample at 3.6 picomole per liter sensitivity, approximately $10^{-18}$ moles of analyte could be theoretically detected. This is within or beyond the range required for DNA and RNA probe assays, where post replication detection of $10^7$ to $10^9$ molecules is desired. In an assay for DNA or RNA, or generally, polynucleotides, a given strand and its complementary strand would constitute the binding pair. For some assays it would be sufficient to utilize only the last enzyme in the cascade, thrombin. In such cases, higher sensitivity would not be required.

In addition to the cascade system, either a steric or exclusion mechanism is chosen to couple the signal generated from the binding pair into the coagulation cascade. If a steric mechanism is chosen, a homogeneous assay will result; that is, separation of free and bound analyte will not be necessary as an operator step or as a step performed by the instrument. The steric mechanism is typically chosen for analytes of low molecular weight. The exclusion mechanism, utilizes a separation of free from bound analyte internal to the reaction slide and without wash steps. This approach is typically chosen for analytes of high molecular weight or for cellular elements.

In addition to the options of steric or exclusion coupling mechanisms, the cascade reaction can be initiated in two ways: by simple entry of the initiation molecule into a chamber containing reaction components for the cascade, or by the use of a triggerable initiator. A triggerable initiator can be placed in contact with or moved into contact with reaction components for the cascade and not undergo any reaction until it is activated or "triggered" by the use of external energy input, such as in the form of ultra violet light or thermal pulse or step function. Use of a triggerable initiator allows complete mixing to be achieved before the cascade reaction is initiated, thereby providing assays with even greater precision, when required, and simplification.

As noted above, the present method may be used to assay a wide variety of species. These may be generally grouped into three classes: (1) Low molecular weight species ($\leq 2,000$ daltons), and (2) High molecular weight species (>2,000 daltons) and cellular elements. Each of these is described below.

I. Assay of Low Molecular Weight Species (<2,000 daltons)

Figure 5A:
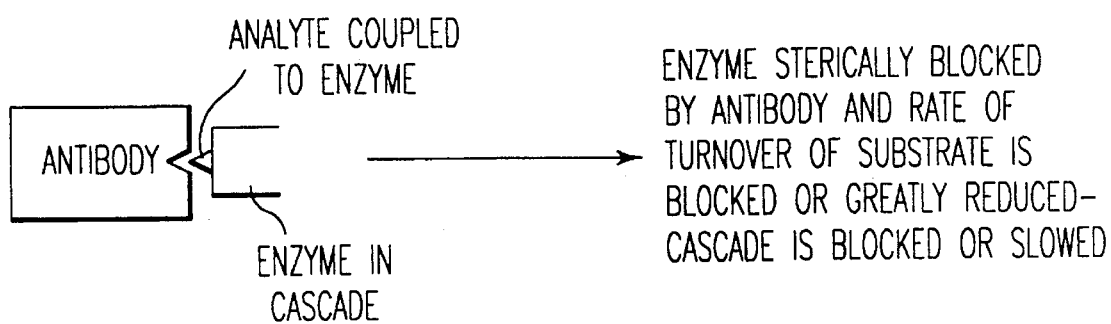
FIG. 5 provides a schematic depiction of a steric assay strategy that can be used in the present binding pair assay method.
Figure 5B:
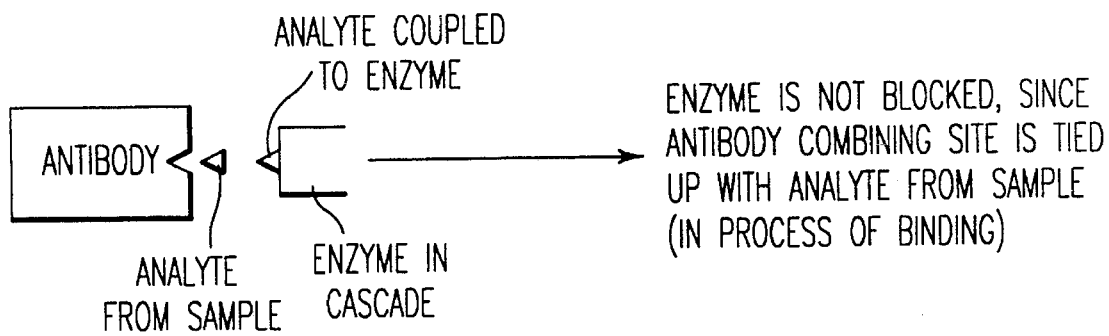
Figure 6A:
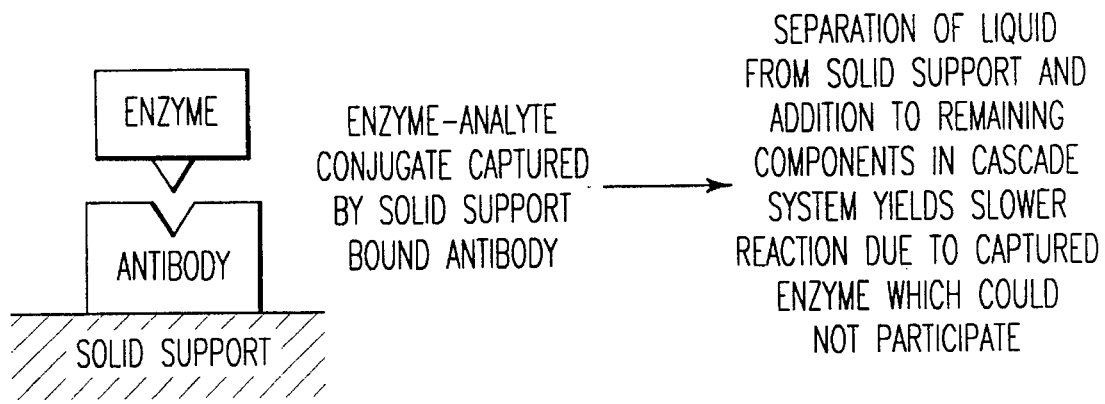
FIG. 6 provides a schematic depiction of an exclusion assay strategy that can be used in the present binding pair assay method.
Figure 6B:
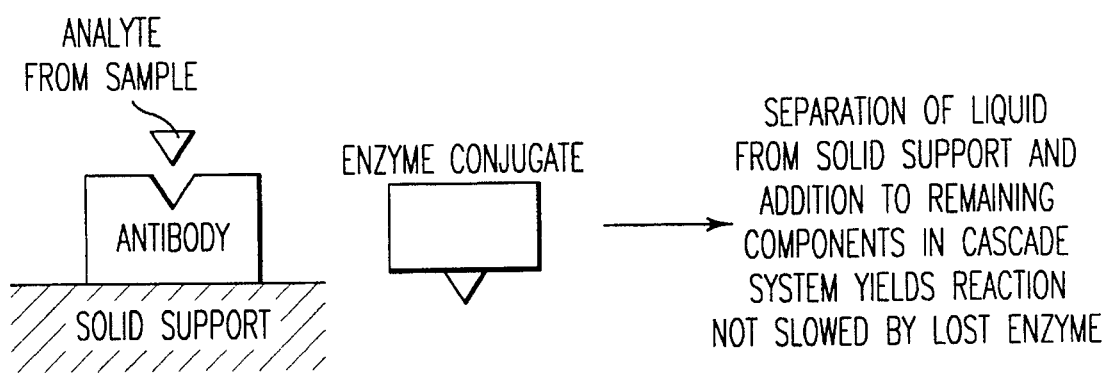

In this embodiment, either a steric or exclusion mechanism is chosen to transmit the signal from the binding pair into the system. In a steric mechanism utilizing analyte-initiator conjugate, a homogeneous assay will result if steric interference with initiator function occurs after the binding pair reaction. If the initiator is instead attached chemically to the non-analyte member of the binding pair, a steric mechanism could be utilized, provided that the chemical attachment of the initiator is close to the binding site on the non-analyte member of the binding pair and steric hindrance of initiator function occurs upon binding of analyte to its binding pair complement. FIGS. 5 and 6 present a schematic depiction of the steric and exclusion mechanisms.

Steric Mechanism: In the steric assay strategy, either a free (unbound) binding pair partner of the analyte is used in the dry reagent along with the initiator, which is chemically coupled to a replica of the analyte (reactive with its complementary binding pair partner) or, alternatively, only initiator chemically coupled to the binding pair partner of the analyte is utilized. After addition of the sample of interest and incubation for a predetermined time, the initiator is activated by energy input, such as heat or light.

During the incubation period, if the sample contains none of the analyte of interest, the analyte replica coupled to the initiator reacts with the corresponding binding pair partner. This reaction thus sterically blocks the activated initiator from beginning the cascade reaction and thus the cascade is blocked or greatly slowed. Alternatively, if the initiator is coupled to the binding pair partner of the analyte, and if the sample does not contain the analyte, the initiator is not sterically hindered, and thus the cascase reaction is initiated and proceeds quickly.

However, if the sample contains the analyte of interest, this free analyte effectively competes with the initiator-bound analyte for reaction with its binding pair partner during the incubation period. Thus upon activation of the initiator, the initiator containing bound analyte, which has not reacted with the its binding pair partner, is then free to initiate the cascade reaction. The rate of the cascade reaction is then proportional to the amount of active unblocked initiator, or directly proportional to the amount of analyte present in the sample. Thus, the higher the level of analyte in the sample, the faster the cascade reaction occurs and vice versa.

Alternatively, if the binding pair partner of the analyte conjugated to the initiator is utilized in the dry reagent, sample analyte, when present, reacts with the binding pair partner, attaching thereto and thus sterically hinders the initiator, when activated or triggered, preventing it from starting the cascade reaction. In this embodiment, the resulting rate of cascade reaction after addition of analyte from the sample and subsequent activation of initiator is then inversely proportional to the amount of analyte present in the sample. Thus, in this case, the higher the level of analyte in the sample, the slower the cascade reaction occurs and vice versa.

Exclusion Mechanism: In the exclusion assay strategy, a solid support-bound analyte binding pair partner is typically utilized. For example, the binding pair partner may be covalently bound to a surface in the reaction slide reaction chamber or to the magnetic particles used to perform mixing, or to other, nonmagnetic particles (e.g., glass beads) that can be driven into suspension rapidly by the magnetic particles when the magnetic field is applied. The dry reagent system used thus contains, for example, the bound antibody, along with the same type of analyte-bound initiator as in the steric assay strategy. After the sample has been added to the reaction slide containing the dry reagent, and the reaction incubated, the liquid reaction solution is separated from the solid support, added to the remaining components of the cascade system and the cascade reaction time measured.

If the sample of interest contains no free analyte, the analyte-bound initiator reacts with its surface-attached binding pair partner during the incubation period. Upon separation of the liquid from the solid support and addition of the liquid to the remaining components of the cascade reaction system, the cascade reaction is seen to be greatly reduced or even stopped, due to the capture of the analyte-bound initiator by the antibody bound to the solid support.

However, if the sample of interest contains free analyte, the free analyte effectively competes with the analyte conjugated to the initiator for reaction with the bound antibody. Thus, when the liquid is separated from the solid support and added to the remaining components of the cascade, the cascade reaction proceeds at a rate that is proportional to the amount of initiator present in the liquid, or directly proportional to the level of free analyte in the original sample.

It should be noted that there are many ways to achieve separation of the liquid from the solid support using the reaction slide technology. Typically, liquid would be moved by capillary action upon opening a valve or vent or by being physically pumped due to the pressure of a piston on the flexible top of the reaction chamber or by means of pressure or vacuum pumping resulting from moving an orifice connected to a pressure or vacuum source into contact with an appropriate orifice on the reaction slide. Some of these methods are discussed in the present text. Others may be found in U.S. Pat. No. 4,849,340. Magnetic particles in a first chamber may be prevented from moving with the liquid transported into a second reaction chamber by application of a magnetic field at the right moment and maintaining that field until transport is completed.

In an alternative embodiment of the use of the exclusion mechanism for detection of low molecular weight analytes, an analyte replica could be attached directly or through a linker molecule to a solid support and the binding pair partner conjugated to the initiator. In this embodiment analyte binds to the initiator-binding partner conjugate, allowing the conjugate to remain in solution and thereby prevent its binding to the solid support attached analyte. Thus, when liquid is separated from the solid support and added to the remaining components of the cascade, the cascade reaction proceeds at a rate that is proportional to the amount of initiator present in the liquid or directly proportional to the level of sample analyte in the original sample.

Another method of implementation of the exclusion mechanism is to separate the liquid contents of the reaction chamber using a liquid absorption module (or LAM). This is an absorbent member brought into contact with the air vent portion of the reaction chamber. (See U.S. Pat. No. 4,849, 340.) The extraction of liquid from the reaction chamber is optionally followed by a wash step, which may be conveniently performed by the instrument, whereupon the cascade reaction is then started, triggered by bound initiator containing conjugates in the reaction chamber after additional cascade components are added in a final step. This method of implementation, however, generally involves more steps and is not preferred.

In the present method, an excess of all cascade components must be present so that the rate limiting component is the initiator component coupled to one member of the binding pair reaction. For example, if the human blood coagulation cascade is chosen as the basis for the system, then all additional cascade components, such as enzymes, cofactors, substrates, and activators, should be present in large excess to prevent deficiencies of these same components from the sample from influencing the reaction. Furthermore, natural inhibitors, which may exist in the sample, can be neutralized by agents contained in the dry reagent formulation. Alternatively, natural inhibitors can be effectively neutralized by diluting all samples by a fixed amount prior to performing the assay. This strategy adds an extra step, however, and lowers the analyte detection sensitivity by an amount equal to the dilution factor.

The first component in the cascade system, called the initiator, must be chosen such that it is never present in the sample in free form. For example, Factor X, the precursor to Factor $X_a$, and prothrombin, the precursor to thrombin, are normally present in blood. However, neither Factor $X_a$ nor thrombin is normally present in a blood sample. If either thrombin or $X_a$ are present, they are bound to natural inhibitors in the blood and are thus inactive. Thus, both Factor $X_a$ and thrombin are suitable initiators for use in the present method when the blood coagulation cascade system is used.

In the reagent, the initiator is chemically conjugated or covalently coupled via linkers to one member of the binding pair to create the conjugate form of that member of the binding pair. In some cases, primarily when the exclusion mechanism is utilized, the initiator may be held at a distance from the analyte or binding pair partner by being coupled to a long linker (e.g., linkage such as biotin-avidin). In other cases, the initiator may be held in close proximity to the analyte or binding pair partner. In all cases, a conjugate form is utilized. The extent of reaction of this conjugate in the binding pair reaction is thus transmitted to the cascade reaction by means of either the steric or exclusion mechanisms to create the assay measurement. Moreover, in this invention, this conjugate is contained in a dry chemistry formulation containing magnetic particles, which are preferably substantially homogeneously mixed therethrough. In certain cases, it may be desirable to separate analyte and binding partner in the same dry chemistry to avoid interaction prior to addition of the sample. In these cases, analyte and binding partner may be physically separated in the reaction chamber. However, it may also be desirable in certain cases to intentionally react the analyte replica and its binding partner prior to conversion to a dry chemistry format. This will still enable displacement of replica by sample analyte during the performance of the assay and may decrease nonspecific binding by nonanalyte species at the expense of extending reaction time and possibly requiring increased convective mixing. Contained also in this dry chemistry formulation may be buffers and possibly other components of the cascade system, as discussed above.

The initiator and its conjugated binding pair member can be utilized in the assay system in multiple ways.

In a preferred embodiment, a triggerable initiator is employed. A triggerable initiator is one that, although normally not present in the sample, is contained in the reagent in an inactive form and can be activated by input of energy, such as by a thermal pulse or thermal step function, by a photonic (light energy, i.e., visible, ultraviolet, or infrared) pulse or step function or by electrical energy, sonic energy, or other energy input sufficient to convert the initiator into an active form after a predetermined incubation period. The use of a triggerable initiator is an improvement allowing better separation of the affinity reaction from the cascade reaction, in effect allowing these reactions to be performed sequentially. In the present invention, the triggerable initiator may be, for example, a modified enzyme selected from the components of the cascade system used. The modified enzyme may be located early in the cascade system or late in the cascade system.

In one embodiment, the triggerable initiator is attached to one member of the assay binding pair. After incubation to allow interaction between the members of the binding pair, the initiator is then triggered to start the cascade reaction, with the initiator being the starting point for the cascade. This starting point may be any of the enzymes of the cascade reaction.

In an alternative embodiment, the enzyme bound to one member of the binding pair is a zymogen, such as prothrombin, which requires the next higher enzyme in the cascade to cause the cascade reaction to occur. In this embodiment, the triggerable initiator can be any one of the enzymes higher in the cascade than the zymogen bound to the member of the binding pair. Once again, the cascade reaction will start upon triggering of the initiator into an active enzyme of the cascade.

As examples of suitable triggerable initiators, there are enzymes that become activated upon changing the pH in a very narrow range (see Mahler and Cordes, Biological Chemistry, Harper and Row, N.Y., 1966, pp. 263–267). It is also known that enzymes generally exhibit an optimum pH and an optimum temperature for their enzymatic reactions (Mahler and Cordes, pp. 263–277). Changes in the thermodynamics of substrate binding may occur for wild type and engineered mutants of enzymes. Extreme curvature is frequently found in Arrhenius plots for enzymatic reactions and can arise from changes with temperature in the rate determining step or gross properties of the enzyme solvent interaction. Mutation may cause energetic changes due to enzyme solvent shell or local structure (Wells. et al Biochemistry, 1991, 30, 5151–5156).

Enzymes may become considerably more active upon elevation of the temperature beyond a certain threshold. Below this threshold, the enzymes are considerably less active and cannot process their respective substrate molecules at a meaningful rate. Chemical modification of enzymes has yielded forms that are known to become active (or inactive) by cleavage of the chemically modifying group upon exposure to light of sufficient intensity at a given wavelength (see Porter et al. J. Am. Chem. Soc., (1989), 111, 7616; Biochem. (1990), 29, 4871 and 8042; Photochem. and Photobiol. (1990), 51, 37–43; see also Porter et al. U.S. Pat. No. 5,114,851). However, the use of such chemically modified enzymes would introduce the product of cleavage into the reaction medium and thus possibly interfere with the cascade reaction of the present invention or with the measurement of the cascade time. Enzymes that are inactivated, or activated by the addition of chemical reagents or in certain pH ranges are also known, but these are less useful and not as practical as triggers because they require introduction of additional chemical constituents which may affect the binding pair reaction and measurement of the analyte and require additional steps (see Blake et al. Clin. Chem. (1984), 30/9, 1452–1456; Siddigi et al. U.S. Pat. No. 4,960, 693; Toyomaki et al. U.S. Pat. No. 4,985,354; Enomoto U.S. Pat. No. 5,093,237; and Hall et al. European patent application 0,123,265).

In a triggerable initiator based system of the present invention, the binding pair members in sample and reagent are free to interact during an initial incubation period after the sample is added to the dry reagent. Forced convective mixing can be utilized at this time, preferably by oscillation or circular translation of the magnetic particles, to allow the binding pair reaction to proceed, to a near equilibrium condition if desired, before triggering the initiator and starting the cascade reaction. At a predetermined time, this triggering process can be performed automatically by the testing instrument.

Another embodiment uses the initiator in a nontriggerable format. In this case, a two step or two compartment assay results. After incubation of sample and initiator-binding-pair-member-conjugate with forced convective mixing for a preset time, preferably by oscillation or rotation of the magnetic particles, the reaction mixture is sent via capillary action or pumping into a second chamber, where the remaining components of the coagulation cascade system are present in dry form along with magnetic particles, preferably essentially homogeneously mixed therethrough. Although not required, it is preferred that the magnetic particles used for mixing in the first chamber be retained magnetically in that chamber and only the sample moved into the second chamber when initiated to do so by the instrument. Inhibitors in the first chamber, such as heparin, prevent the initiator from starting the cascade reaction. Inhibitors from the first chamber are then neutralized in the second chamber. For example, heparin would be neutralized with polybrene or protamine. The magnetic particles are then interrogated by the use of an oscillating or rotating magnetic field and photodetector. The photodetector is preferably used with a light emitting diode source, most preferably a diode source that emits at 900 nanometers. The coagulation reaction proceeds, ending in a gel formation. The clotting time or other features of the curve associated with fibrin clot formation may be used as the endpoint or kinetic rate measurement. The clotting time as indicated by the time to reach peak oscillation for an oscillating system would be used. Such use of magnetic particles in determining blood coagulation times can be performed in accordance with the process described in U.S. Pat. Nos. 4,849,340 and 5,110,727 to Oberhardt, the portions of which relate to measurement of coagulation times by interrogation of magnetic particle oscillation and to the instrumentation for performing these measurements are hereby incorporated by reference. Preferably, the clotting time in a highly convective field would be measured as "lift off" from a reaction baseline reflectance measurement in a circular translation system, driven by a rotating magnetic field. In this case, the magnetic particles tend to aggregate as the clotting time endpoint is reached.

In the triggerable system, all components would preferably be situated in a dry chemistry mixture in a single reaction chamber containing magnetic particles. This is the preferred embodiment and also the simplest system, allowing measurement and all reactions to occur in the same chamber. As in the previous case, the coagulation would be read as a clotting time.

As another embodiment, a lysis onset time instead of a clotting time could be employed (see Oberhardt et al., Dry Reagent Technology for Rapid, Convenient Measurements of Blood Coagulation and Fibrinolysis, *Clin. chem.* 37, 520–526, 1991). However, a lysis based system would be less sensitive due to less cascade amplification.

To determine the analyte concentration, the clotting time or lysis onset time would be read in terms of concentration from a standard curve. This could be automatically performed by the instrument.

The low molecular weight species assay embodiment is exemplified by the description below of an assay for quinidine, a cardiac drug of approximately 324 daltons.

A thermally activatable mutant of Factor $X_a$ is chosen as the initiator, which is coupled to the analyte of interest, quinidine. The quinidine is coupled to the $X_a$ mutant molecule, such that upon incubation with quinidine-specific antibody, the binding of antibody to quinidine sterically interferes with the active site of the $X_a$ mutant. Otherwise the enzyme is unaffected.

A reaction slide is prepared containing the above described $X_a$ mutant - quinidine conjugate, a fixed amount of anti-quinidine antibody, excess prothrombin, fibrinogen, phospholipid, and excess inhibitors (antibodies) to Factors V, Va and platelet factor 3, in combination with HEPES or OWRENS as a buffer and magnetite as magnetic particles. The mixture is added to the reaction volume (or chamber) of the reaction slide and freeze dried to prepare the dry chemistry reaction slide.

To perform the quinidine assay, the reaction slide is placed in the instrument and automatically brought to operating temperature, typically 37° C. for this assay system. A drop of blood is added to the reaction slide and sample well. The blood enters and dissolves the reagent. The magnetic particles are driven into motion by application of an oscillating magnetic field creating convection and mixing the reactants. During this period the anti-quinidine antibody is allowed to bind to the quinidine on the $X_a$ mutant-quinidine conjugate and to quinidine that may be present in the sample. This distribution of the fixed amount of antibody between conjugate and sample quinidine occurs as the reaction is allowed to continue during a predetermined incubation period. At the end of this incubation period, the temperature set point is rapidly increased by 8° C./min to a level at which the $X_a$ mutant undergoes a conformational change and becomes active. At this point, the $X_a$ enzyme begins to convert prothrombin to thrombin at a rate proportional to the concentration of active $X_a$ enzyme. The $X_a$ enzyme sterically inactivated by antibody does not convert prothrombin to thrombin or converts it at an extremely low or negligible rate. Therefore, the concentration of $X_a$-quinidine conjugate that has not reacted with antibody determines the rate of conversion of prothrombin to thrombin. The generated thrombin converts fibrinogen to fibrin, thus amplifying the chemical signal further. When fibrin formation reaches a critical stage, the clot or endpoint is detected by changes in the magnetic particle movement. The elapsed time from thermal triggering to clot endpoint is the clotting time. The clotting time is thus proportional to the quinidine in the sample. The actual quinidine concentration in the sample can be read automatically from a standard curve stored in the measuring instrument for that particular lot of reaction slides. This value can be converted to a plasma quinidine concentration, if desired, by correcting for the fraction of the reaction volume occupied by blood cells. A correction factor for total cell volume, in blood typically equivalent to hematocrit, may be entered into the instrument's computer memory or this conversion may be performed from a simple chart.

II. Assay of High Molecular Weight Species (>2,000 daltons) and Cellular Elements For assay of large molecular weight analytes, polynucleotides, lipoproteins, and cells, yet another embodiment is employed, using enzyme-binding pair conjugate in a system utilizing two binding pair partners of the analyte (i.e. antibodies, receptors, or complementary polynucleotides) where one of the binding pair partners is conjugated to initiator and not attached to any surface and the other is not conjugated to initiator but attached to a surface. Each of the two binding pair partners of the analyte binds to a different region of the analyte, and both can bind to the analyte simultaneously. This embodiment is based on exclusion and triggering. In this system, a first binding pair partner is covalently bound to a solid support. This support could be either the reaction slide base material or the magnetic particles that are subsequently driven into motion to provide convection in the reaction volume. The first binding pair partner is available in excess and binds to one or more regions of the analyte molecule or cell. The second binding pair partner binds to a different region of the analyte molecule or cell. This second binding pair partner is conjugated to a triggerable initiator in the form of a coagulation enzyme. This enzyme is energy activatable, as described above, in a second reaction chamber. Cascade components, such as fibrinogen, calcium, prothrombin, and other components of the blood coagulation cascade system are present in the second chamber in a dry reagent containing magnetic particles, such as $Fe_3O_4$. After a preset incubation time in the first chamber, a vent cover or valve is released to allow entry of liquid into the second chamber. If the first chamber is a sample well, then the second chamber is actually the first and only capillary chamber. When liquid flows into the capillary chamber, the magnetic particles of the first chamber do not flow with the liquid and are kept stationary via a permanent magnet or D.C. electromagnetic field. Therefore, only unbound second binding pair partner molecules can enter the capillary chamber. This binding pair partner is conjugated to the initiator, or coagulation enzyme such as Factor $X_a$ in the case of the blood coagulation cascade, which is held inactive until triggered. The enzyme is then triggered by application of energy, such as by heat or ultraviolet light, thus initiating the coagulation cascade. The clotting time is thus inversely proportional to the remaining free concentration of the now active initiator and is therefore directly proportional to the concentration of analyte. The analyte concentration is then read off of a standard curve using the resultant clotting time.

The high molecular weight species embodiment is exemplified in the descriptions below of assays for Apolipoprotein B-100, a large lipoprotein molecule associated with atherosclerosis risk, and for CKMB, a marker of acute myocardial infarction.

Apolipoprotein B Assay: A two chamber dry reaction slide is prepared with a connecting valve or vent cover, so that liquid from the first chamber can be transferred upon command by the instrument into the second chamber (a reaction slide such as this can be found in U.S. Pat. Nos. 4,849,340 and 5,110,727 to Oberhardt, which have already been incorporated by reference). In the first chamber is a dry chemistry mixture consisting of a preset amount of thrombin conjugated to a monoclonal antibody with specificity toward a particular epitope of the Apolipoprotein B-100 (Apo B) molecule and magnetic particles containing covalently bound polyclonal antibody with specificity toward different epitopes on the Apo B molecule than that targeted by the monoclonal antibody. The thrombin is chemically inactivated, but can be activated by irradiation with ultraviolet light. The polyclonal antibody is in large excess, distributed over the very large surface area of the particles. In the second chamber is a dry chemistry reagent consisting of fibrinogen, magnetic particles with no antibody or other agent coupled to them and a buffer, such as HEPES. To create the dry chemistry reagent, each reaction chamber is filled with liquid reagent mixture and the entire reaction slide freeze dried.

To perform an assay for Apo B, the reaction slide is placed in the analyzer instrument and both chambers brought automatically to a consistent temperature of 37° C. The sample is then applied in excess to the sample well, filling the first chamber and solubilizing the dry reagent. A rotating magnetic field drives the particles into convective mixing, and continues to mix for a preset incubation time. During this time, the antibody on the particles binds essentially all Apo B in the sample. Simultaneously, a portion of the thrombin-antibody conjugate binds selectively to Apo B in proportion to the number of Apo B molecules present. The Apo B is thus doubly bound. When the preset incubation time period has ended, the vent cover is lifted, or the valve activated, allowing the reaction liquid to move into the second chamber. The magnetic particles are held back by activation of a D.C. electromagnet in the region below the first chamber. Liquid containing free thrombin-antibody conjugate then moves into the second chamber, solubilizing the second dry reagent. The magnetic particles in the second chamber are driven into a convective mode by a rotating magnetic field for a short preset time, and then a step function of ultraviolet light is delivered to the second chamber of the reaction slide from an internal UV lamp, or alternatively, by a series of flashes from an internal flash tube. At this point in time, the thrombin is activated, initiating the final step in the coagulation cascade of fibrinogen conversion to fibrin. The moving magnetic particles are monitored at 900 nanometers by the photodetector and associated signal processing circuitry. The particle motion signature allows precise determination of the clotting endpoint. The elapsed time, from UV irradiation to clotting endpoint is proportional to the Apo B concentration in the sample and can be read from a standard curve.

CKMB Assay: A reaction slide containing two chamber dry chemistry reagent is prepared with a connecting valve or vent cover, so that liquid from the first chamber can be transferred upon command by the analytical instrument into a second chamber. In the first chamber is a dry chemistry reagent mixture consisting of a large excess of antibody specific for the "B" region of the cardiac muscle protein CKMB. The antibody is covalently bound to magnetic iron oxide ($Fe_3O_4$) particles, such that a significant portion of the surface area of each particle is coated with antibody. The remaining particle surface is "blocked" or passively neutralized from participating in binding reactions. Blocking may be achieved by coating the remaining surface area with bovine serum albumin (BSA), casein, or other proteins that do not participate in the reaction of interest. In addition to the particle-bound antibody to the B-region of CKMB, a specific amount of a second antibody to the M-region is also present in the form of a conjugate. This conjugate consists of the M-region specific antibody covalently bound to Russell's viper venom (RVV). RVV is snake venom which converts clotting factor X to $X_a$. This reaction rate is increased in the presence of Factor V. The sample can contain CKMB (cardiac muscle type) but also the interfering substances CKMM (skeletal muscle type) and CKBB (brain type). The assay for CKMB in the presence of CKMM and CKBB can be performed with the following procedure.

The sample is introduced into the first chamber, which is a capillary chamber. The sample can be a plasma, serum, or whole blood sample. Preferably, the sample is diluted with buffer or control plasma prior to application to the first chamber to normalize the coagulation cascade inhibitors present. When the sample enters the first chamber, the reagents become solubilized, and the magnetic particles are free to move in a magnetic field rotating at 180–3600 RPM. This produces substantial convection and enhances the binding of CKMB and CKBB to the B-specific antibody on the particles. The M-specific antibody -RVV conjugate binds to CKMB, which becomes attached to the particle bound CKMM and also to the soluble CKMM. Convection is allowed to continue for a preset time. Then, a vent cover is automatically opened or lifted, or a valve opened, by the instrument, allowing a portion of the reaction liquid to enter and fill the second chamber, which is preferably smaller in volume than the first chamber. The magnetic particles in the first chamber are held back by the rotating field or alternatively are brought down to the base of the first reaction chamber by activation of a D.C. magnetic field.

In the second chamber, the reaction liquid rapidly solubilizes the dry reagent consisting of Clotting Factor X, Factor V, Phospholipid, prothrombin, calcium, fibrinogen, a buffer such as HEPES or OWRENS, and magnetic iron oxide particles, which may be uncoated or blocked, such as by coating with BSA. The magnetic particles are driven into motion by either a rotating magnetic field or an oscillating magnetic field. The moving magnetic particles are monitored by a photodetector and illuminated at 900 nanometers by a light emitting diode. The particle motion allows precise determination of the clotting endpoint. The clotting time varies inversely with the concentration of antibody conjugated RVV that is present in the liquid entering the second reaction chamber. This antibody-conjugated RVV may exist in unbound form, or may be bound to CKMM molecules. The antibody conjugated RVV that does not enter the second chamber is that which is bound to the CKMB (but not CKBB) molecules captured by the first B-region specific antibody on the magnetic particles. The clotting time measured in the second chamber is therefore directly related to the concentration of CKMB in the sample.

In the above type of assay for CKMB, the assay can alternatively be performed with an $X_a$ molecule or a $X_a$ molecule that is inhibited from functioning as an enzyme until exposed to ultraviolet light. This triggering would be performed in the second reaction chamber after the dry chemistry reagents are dissolved and well mixed, and can provide an assay of greater precision and reproducibility.

The 2-chamber assays described above can be performed using a diluted sample, such as diluted serum, plasma or whole blood. This is a different strategy than that used in the quinidine assay example in order to minimize differences in clotting factors among individual patient samples.

In the assays described above, a pooled plasma sample can be employed as a dry reagent, instead of using individual clotting factors such as X, V, phospholipid, prothrombin, and fibrinogen.

Figure 11B:
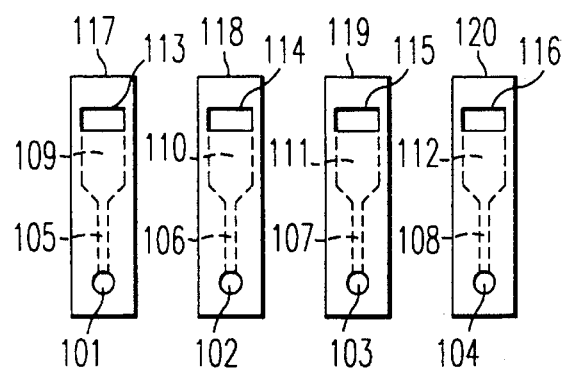
Figure 11B:
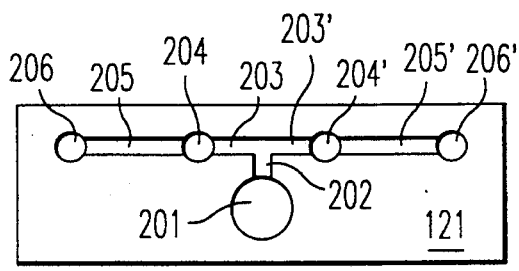
Figure 11B:
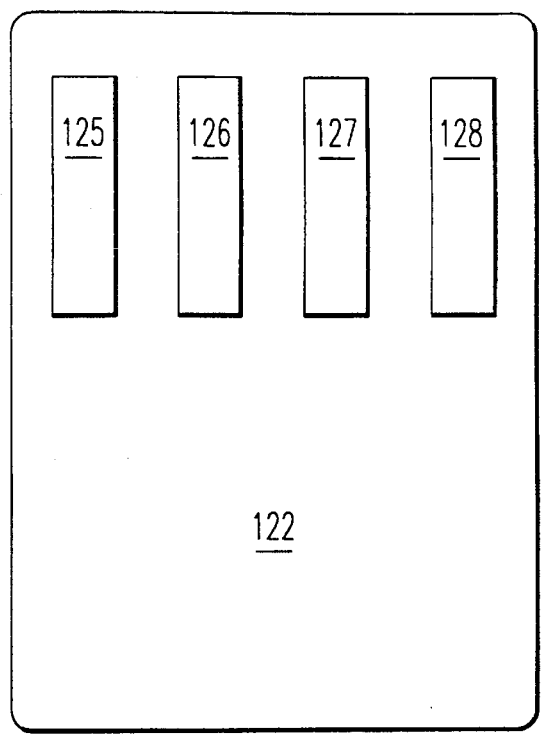
Figure 11B:
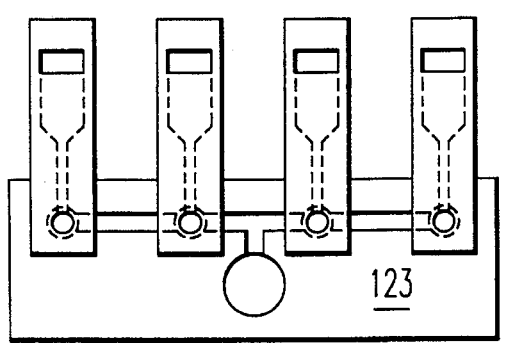

When it is desired to provide an assay panel, such as in screening for atherosclerosis, providing a test for myocardial infarction, etc., it is often necessary to utilize reaction elements containing different reagents in combination. It is a significant challenge to combine reaction elements, which may require different reaction components, different durations of drying, different temperature in dry chemistry preparation, etc. One way to achieve a panel test is to individually prepare and process individual reaction slide elements in accordance with the specifications of their conventional independent production processes and to later recombine them into a combined format, allowing a common sample well to initiate all tests in the panel. This is achieved as illustrated in FIGS. 11A, B, and C. In FIG. 11A, reaction slides 117, 118, 119, and 120 are ready to be combined with connector element 121 and carrier card 122. The connector element 121, when combined with the reaction slides, is depicted in FIG. 11B. The sample well (1) is situated at the upper surface of connector element 121, the outlet ports (206, 204, 204' and 206' in FIG. 11A) are situated on the lower surface of 121 and interface with sample inlet ports 101, 102, 103, and 104 on the upper surface of reaction slides 117, 118, 119, and 120, respectively. The outlet ports are interfaced with the inlet ports in a fluid tight configuration by bonding the connector element 121 lower surface to the upper surfaces of the individual reaction slides (117, 118, 119, and 120). The reaction slide elements may be individually fitted into slots (125, 126, 127, and 128) on carrier card 122 and mounted directly to the card using ultrasonic welding, solvent bonding, adhesive, etc. The final assembly (124) would include the connector element (121) also mounted directly to the carrier card (122) in a similar manner.

Figure 11C:
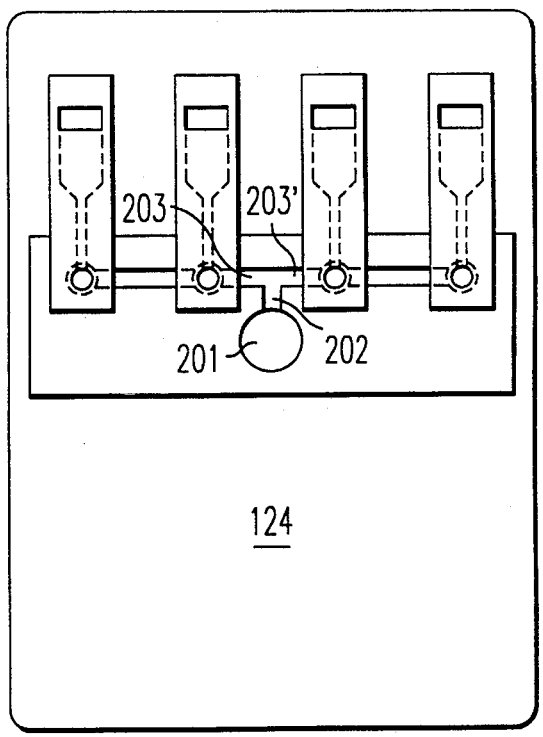

In the final configuration in FIG. 11C, panels may be easily run. When a sample is added to sample well 201, it moves (either by capillary action, pressure, vacuum, or syringe fill) onto conduit 202, then bifurcates to conduits 203 and 203',0and onto outlet ports 204 and 204', conduits 205 and 205', and 206 and 206'. At outlet ports 204 and 204' sample will enter inlet ports 102 and 103, proceed through conduits 106 and 107, respectively, on reaction slides 118 and 119 and fill the respective reaction chambers, 110 and 111, with flow stopping at air vents 114 and 115 (which may be covered with hydrophobic membranes —not shown—if capillary action is not employed as a driving force to fill the reaction slides). Similarly, sample filling conduits 205 and 205' will proceed to outlet ports 206 and 206' and traverse courses through regions 101, 105, and 109, stopping at 113 and 104, 108, and 112, stopping at 116 in reaction slides 117 and 120, respectively.

In other prior art applications of lyophilization, it has been difficult or impossible to achieve multitest or panel capability while at the same time providing for processing and drying of assay chemistries on an individual basis (for example, see Schembi, et al., *Clin. Chem.*, 38/9, 1665–1670 (1992)).

Having generally described this invention, a further understanding can be obtained by reference to certain specific examples that are provided herein for purposes of illustration only and are not intended to be limiting unless otherwise specified.

EXAMPLES

1) To illustrate the cascade concept, a reaction slide was formed from plastic film consisting of a 10×8×0.178 mm rectangular capillary space with an 8×3 mm vent opening adjacent to one end and a 9 mm neck region tapering to 2 mm at the other end opening into a circular sample well of 6.5 mm diameter. The base was opaque and white, the cover and spacer transparent. Base and cover were 0.25 mm thick and the spacer 0.178 mm thick. The empty reaction slide was placed in an instrument to measure magnetic particle ensemble movement by light scatter/reflectance at 900 nanometers using an LED light source with peak light output at 900 nanometers and a photodetector and D.C. amplifier.

An oscillating magnetic field was generated by utilizing a U-shaped alnico magnet of 700 gauss with two 6.35 mm area pole pieces facing the reaction slide. The magnet was attached to the shaft of a D.C. motor via a hole drilled in the magnet's center, allowing it to spin at 2400 RPM about its central axis. The pole pieces were situated at a distance of 5 mm underneath the reaction slide base. The temperature of the reaction slide was maintained at 37° C. by means of an electrical strip heater situated between the magnet and reaction slide.

With this arrangement, blood coagulation reactions can be measured, since coalescence of the suspended magnetic iron oxide particles and entrapment in the fibrin clot yields a progressive decrease in the light scatter and absorption and consequently an increase in background reflectance from the card base.

A dry chemistry reaction slide was prepared by placing a suspension of 7 mg/ml of $Fe_3O_4$ (magnetic iron oxide) of 0.3 micron average particle diameter in 0.5% bovine serum albumin (BSA), 10 millimolar calcium chloride and 0.1% 3,400 dalton polyethylene glycol (PEG) in the reaction volume of the reaction slide and freezing at −195° C. in liquid nitrogen. The reaction slides prepared in this way were then lyophilized in a freeze drier with an initial shelf temperature of −45° C. The resulting dried reaction slides were bought to room temperature and packaged in Ziplock baggies containing desiccant and stored at 4° C. until use.

Figure 7:
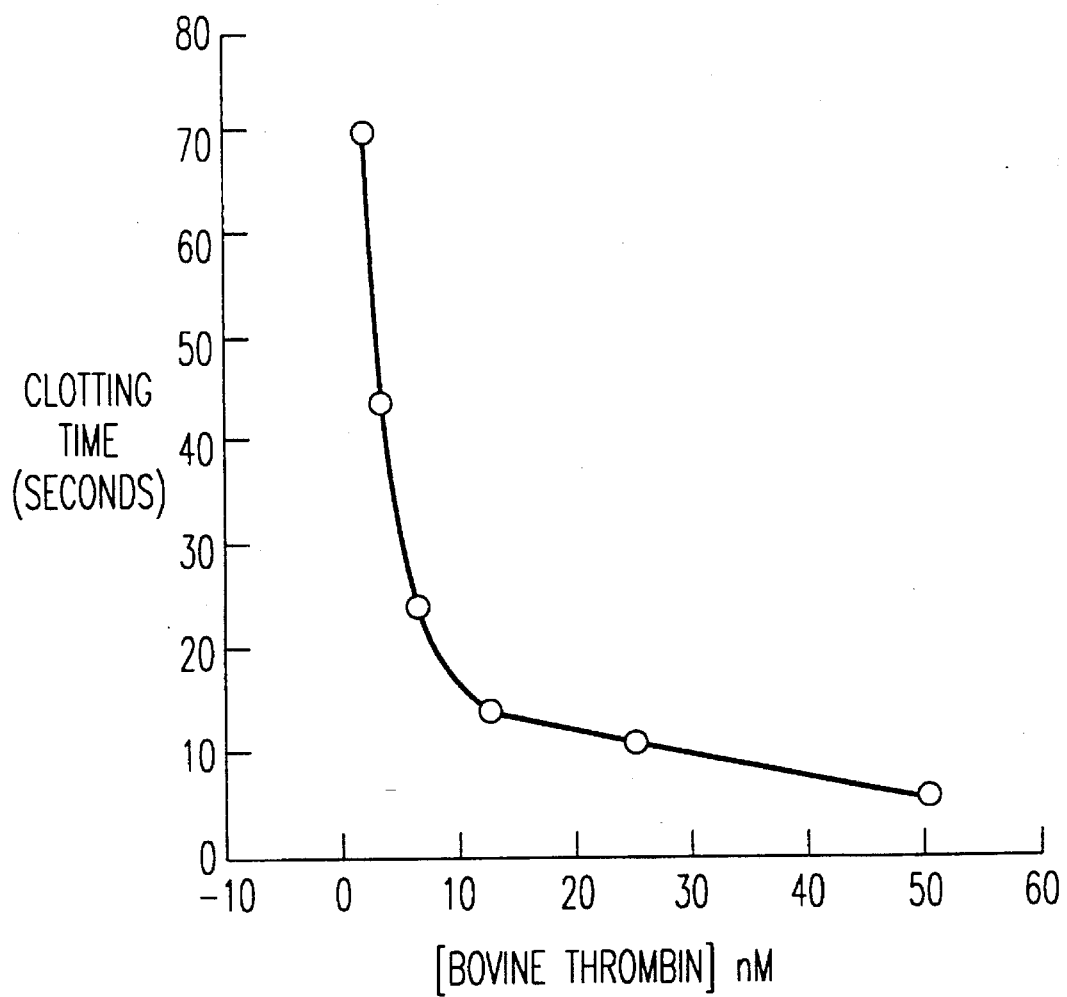
FIG. 7 shows a standard curve for bovine thrombin obtained using the reaction slide technology with magnetic particles, as in Example 1.

To demonstrate the sensitivity achievable with the use of a coagulation cascade system in a magnetic particle interrogation system in the absence of an immunological "front end", the cascade reaction was tested as follows: 3 microliters of a solution of thrombin in Owrens buffer was added to the neck of a reaction slide. In a second step, 27 microliters of 7.3 micromolar bovine fibrinogen was then added, flushing in the 3 microliters of thrombin solution. Upon entry of the liquid into the reaction chamber, the magnetic particles were released from the dry reagent and swirled around creating substantial mixing. After a time, which was dependent upon the thrombin concentration, the fibrinogen in the plasma clotted. The progress of clotting was measured optically, as previously described, and the endpoint readily determined. FIG. 7 shows a plot of clotting time versus bovine thrombin concentration, indicating that as little as 1 nanomole/liter of thrombin may be detected.

Figure 8A:
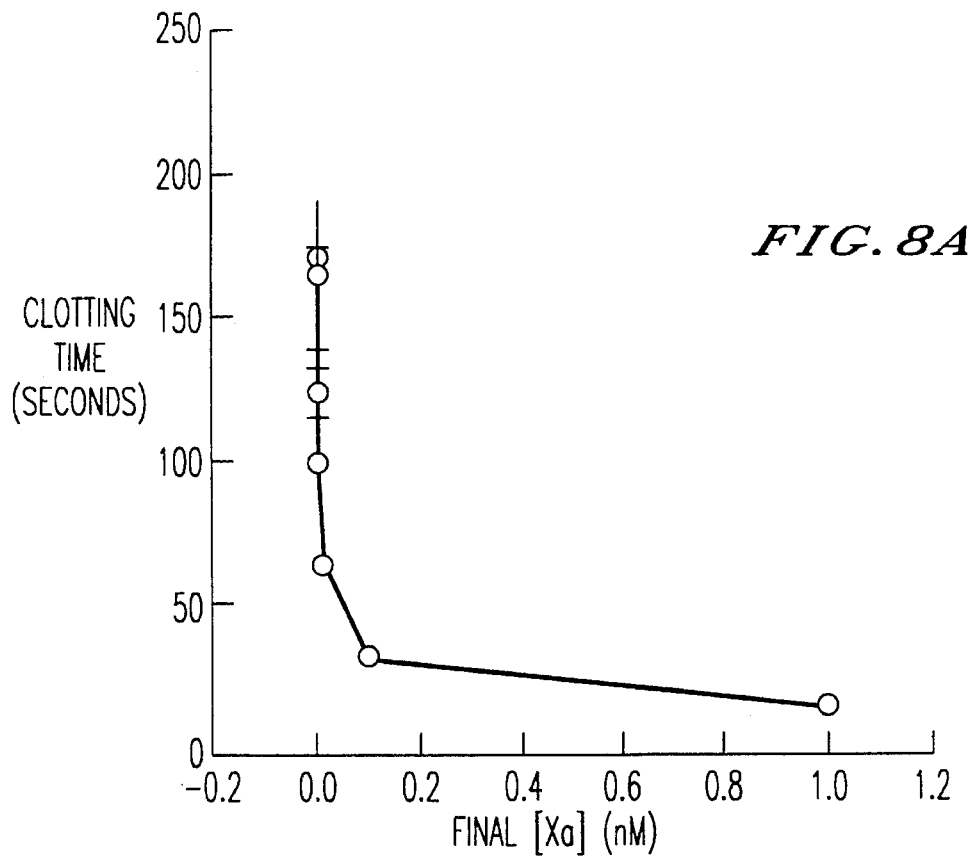
FIGS. 8a and 8b show a standard curve for Factor Xa obtained using the reaction slide technology with magnetic particles, as in Example 2.
Figure 8B:
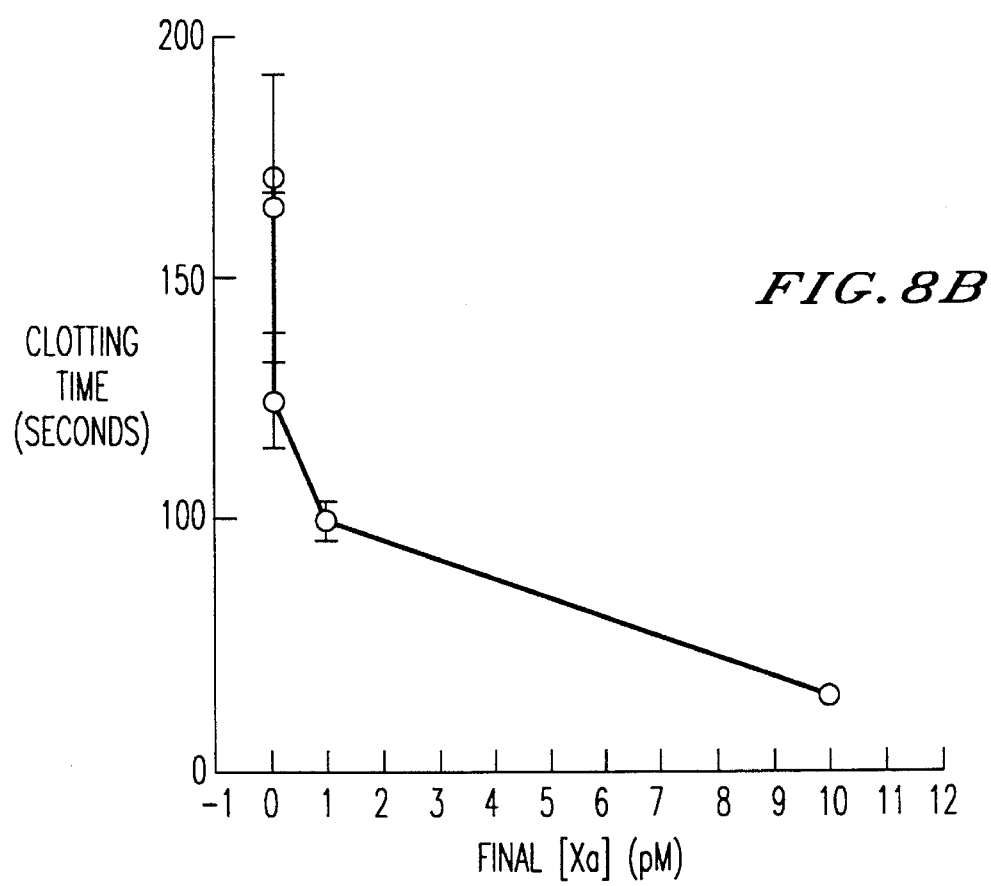

2) To illustrate a 2-step cascade, a reaction slide was prepared as in Example 1, and the same analytical instrument was employed. This time, a solution of Factor Xa in 100 millimolar calcium chloride and OWRENS buffer was used. Three microliters of this solution was pipetted into the neck of a reaction slide. In a second step, 27 microliters of reconstituted, pooled plasma was then added, flushing in the 3 microliters of Xa solution. Upon entry of the liquid into the reaction chamber, the magnetic particles were released from the reagent causing convection. The magnetic particles were used as a means to measure the coagulation endpoint, as previously described. FIGS. 8a and 8b show a plot of clotting time versus Factor Xa concentration. When the added plasma sample contains all cascade components in sufficient concentration, that is, when the lyophilized plasma is fortified with lipid (1:15 rabbit brain cephalin, Sigma Chemical Co.) and 5 micrograms/ml bovine Factor V (Enzyme Research Laboratories, Inc.), the sensitivity is 0.1 picomole of $X_a$ per liter. It is also possible with this system to create a standard curve for the cascade reaction with sensitivity at the lower end equal to approximately 1 nanomole of Xa per liter. This is achieved by minimizing concentration of some cascade components (e.g., factor V)

and will provide enough inherent sensitivity for most immunoassays.

3) To illustrate a 3-step cascade, a reaction slide was prepared as in Example 1, and the same analytical instrument was employed.

Figure 9A:
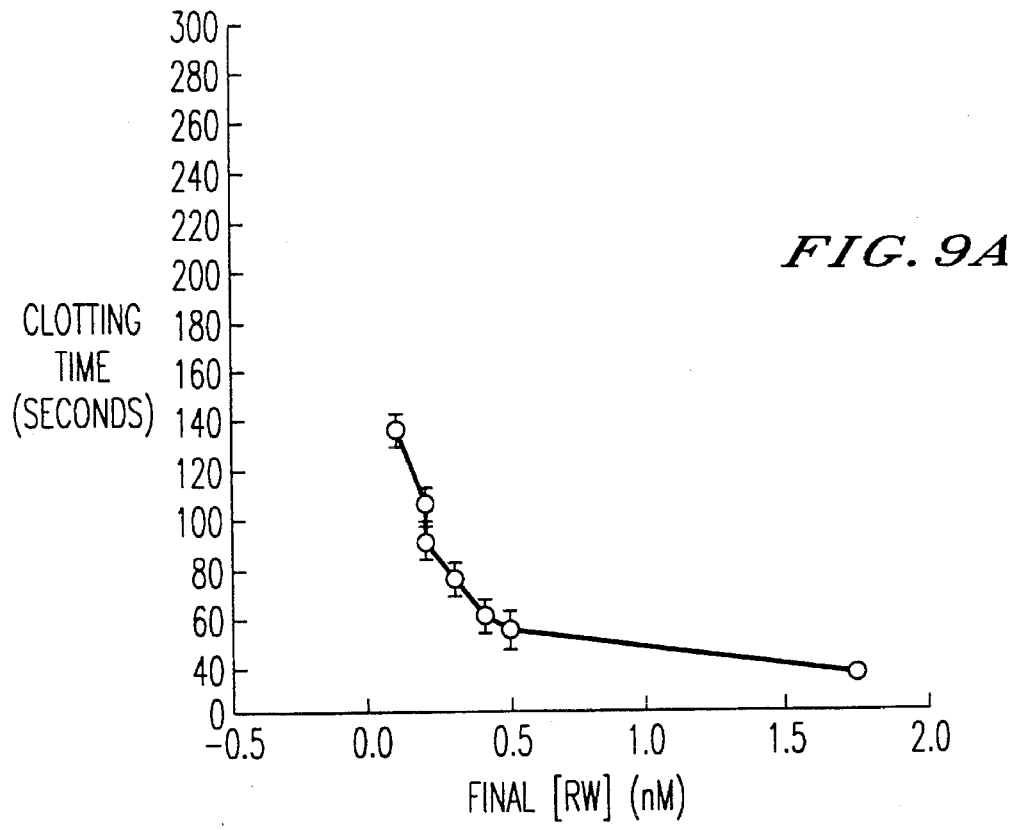
FIGS. 9a and 9b show a standard curve for Russell's viper venom obtained using the reaction slide technology with magnetic particles, as in Example 3.
Figure 9B:
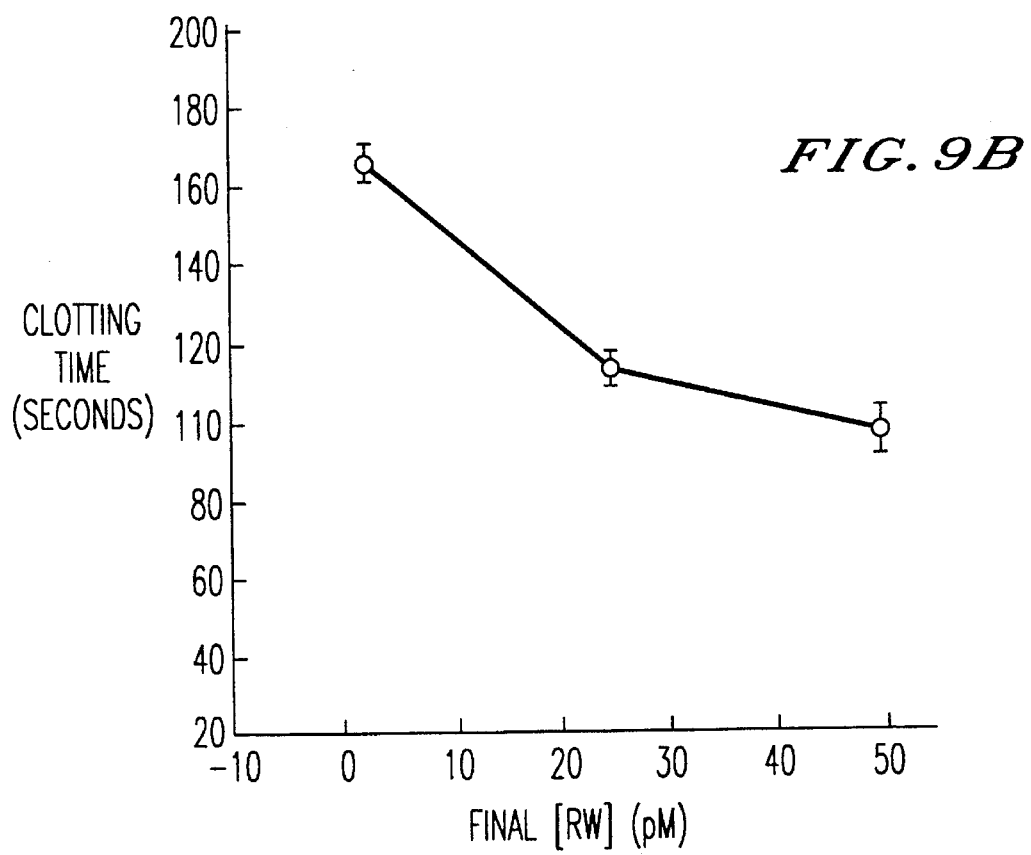

In this example, a solution of Russell's viper venom (RVV) diluted into OWRENS buffer was used. Three microliters of this solution was pipetted into the neck of a reaction slide. In a second step, 27 microliters of reconstituted pooled plasma fortified 1:15 with lipid was then added, flushing in the 3 microliters of RVV solution. From the coagulation endpoint, a standard curve was developed, as in Examples 1 and 2. The final 3 points in the sample dilution curve are shown on a separate graph because they were obtained with a new lot of lipid-fortified plasma. FIGS. 9a and 9b show that it is possible with this system to create a standard curve for the cascade reaction with sensitivity at the lower end equal to approximately 2.5 picomole per liter. This could perhaps be improved by the addition of Factor V to the plasma as in Example 2.

4) To illustrate an example of an inhibited enzyme acting as an initiator, Factor Xa was deactivated with Alpha Methyl-2-hydroxy-4-diethylaminocinnamic acid (AMHDAC). For preparation of this compound, see Porter and Brunhke, *Photochemistry and Photobiology*, 51 (1), 37–43, 1990. The inhibition and photolysis reactions were achieved as follows: Under dim light or darkroom red light conditions, 2 milligrams of AMHDAC was dissolved in 2 milliliters of methyl alcohol. An aliquot of 100 microliters of this solution was added to 900 microliters of 50/50 TRIS/methyl alcohol with 100 millimolar calcium chloride. An aliquot of 202 microliters of this solution was then added to 298 microliters of TRIS with 100 millimolar calcium chloride. One portion of this final solution was added to an equal volume of $1.5 \times 10^{-6}$ molar Factor Xa in OWRENS buffer with 100 millimolar calcium chloride. The final solution contained excess AMHDAC to ensure inhibition of the enzyme. The reaction was assayed in the dark every 30–90 seconds by filling the neck of the reaction slide with 3 microliters of the mixture and subsequently adding 27 microliters of plasma. Complete inhibition was defined as a clotting time greater than 250 seconds. To reactivate, 3 microliters of this solution was placed in the reaction slide of Example 1, followed by 27 microliters of pooled plasma. No clotting reaction was observed. The test card was removed from the instrument and irradiated for 2 seconds with a 365 nanometer 4 watt integrally filtered long wave ultraviolet light tube of 11 cm length and 540 microwatt/cm$^2$ at 6" peak intensity. The light was directed through the flat capillary reaction volume of the reaction slide. The card was immediately returned to the instrument, and the clotting endpoint was measured at 15 seconds.

Thus by combining the use of the magnetic particle interrogation system with a cascade reaction system, for enhanced sensitivity, and an activatable initiator for the cascade system in a binding-pair assay, or immunoassay, one obtains a quick, easy-to-use, assay system that may be performed for example in a doctor's office with results provided before the patient leaves, typically in less than 3 minutes as opposed to hours for commercial immunoassays of comparable sensitivity. Additionally, the sensitivity achieved by the present method is sufficient for essentially all commercial immunoassays and is in a range suitable for other types of binding pair assays.

Figure 10:
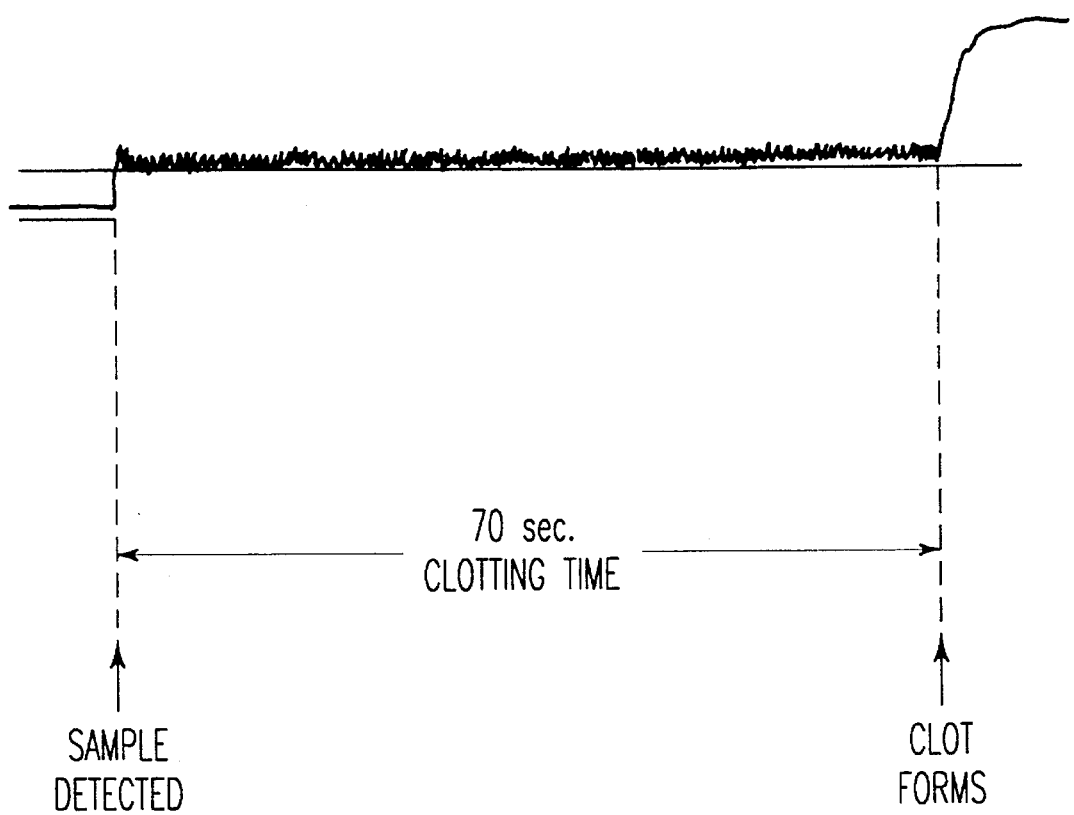
FIG. 10 shows the output from the photodiode amplifier using the apparatus of Example 1 to measure clotting time in assaying Factor Xa from a dry chemistry reaction slide.

5) A reaction slide was prepared as in Example 1, except that in addition to Fe$_3$O$_4$, BSA, and PEG, the solution was adjusted to 10 millimolar in calcium chloride and 32 nanomolar in Factor Xa. The reaction slides were processed as in Example 1 and subsequently tested with the apparatus used in Example 1. In testing, a sample of normal citrated plasma was simply added to the reaction slide sample well in sufficient excess to fill the reaction volume. The resultant waveform is shown in FIG. 10, indicating a clotting time of 70 seconds. At t=0, the sample enters, solubilizing the reagent. At t=70 seconds, the optical signal increases, indicating that the coagulation endpoint has been reached. This response is different from that obtained with oscillating or alternating magnetic fields, where the optical signal decreases at the coagulation endpoint.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters patent of the United States is:

1. A method for performing an affinity assay comprising:
   a) contacting a sample to be assayed for the presence of an analyte with a dry reagent comprising:
      1) an analyte-conjugated initiator comprising said analyte conjugated to a reaction cascade initiator, wherein said reaction cascade initiator is an initiator for a reaction cascade selected from the group consisting of a lytic cascade and a coagulation cascade;
      2) a binding pair partner which specifically binds to said analyte; and
      3) magnetic particles,
   to form an assay mixture comprising (i) said binding pair partner bound to said analyte, (ii) said binding pair partner bound to said analyte-conjugated initiator, and (iii) unbound analyte-conjugated initiator, wherein either a steric or exclusion mechanism is selected to couple a binding pair interaction in said assay mixture with said reaction cascade, wherein:
      in said steric mechanism, when the binding pair partner binds with the analyte-conjugated initiator, the reaction cascade initiator is sterically blocked from initiating the reaction cascade, providing a rate for the reaction cascade which is directly proportional to the amount of unbound analyte-conjugated initiator, and thus directly proportional to amount of said analyte in the sample, and
      in said exclusion mechanism, the binding pair partner that specifically binds with said analyte is bound to a solid support and any analyte present in said sample will compete with analyte-conjugated initiator for reaction with said binding pair partner, wherein initiation of the reaction cascade by said unbound analyte-conjugated initiator provides a rate of the reaction cascade which is directly proportional to the amount of said analyte in the sample;
   b) separating the solid support including (i) said binding pair partner bound to said analyte and (ii) said binding pair partner bound to said analyte-conjugated initiator from (iii) said unbound analyte-conjugated initiator, when said exclusion mechanism is employed;
   c) incubating either (i) said assay mixture when said steric mechanism is employed or (ii) said unbound analyte-conjugated initiator when said exclusion mechanism is employed, with one or more cascade components, to form an incubation mixture, wherein said one or more cascade components is present in an amount sufficient to make initial reaction of said initiator a rate-limiting step in said reaction cascade, wherein said one or more cascade components are sufficient to complete said reaction cascade upon initiation by said initiator, and wherein when said exclusion mechanism is employed, said one or more cascade components are added to said assay mixture after said contacting step, or when said steric mechanism is employed, said one or more cascade components are either present in said dry reagent prior to said contacting step or added to said assay mixture after said contacting step;

d) applying a magnetic field to said assay mixture, wherein said magnetic field is an alternating magnetic field selected from the group consisting of an oscillating magnetic field, a rotating magnetic field and a moving static magnetic field;

e) activating said reaction cascade initiator to initiate said reaction cascade, wherein when said reaction cascade is a coagulation cascade, the coagulation cascade proceeds to formation of a fibrin clot and wherein when said reaction cascade is a lytic cascade, the lytic cascade proceeds by lysis of a fibrin clot;

f) monitoring a response of said magnetic particles to the magnetic field by an optical means to provide a time varying optical signal; and g) determining a concentration of said analyte in said sample by analysis of said time varying optical signal.

2. The method of claim 1, wherein said reaction cascade initiator is activated by exposure to light or heat.

3. The method of claim 1, wherein said reaction cascade initiator is activated by transferring said assay mixture, when said steric mechanism is employed, or said unbound analyte conjugated initiator, when said exclusion mechanism is employed, from a first portion of said reaction chamber to a second portion of said reaction chamber, wherein one or more inhibitors are present in said first portion to prevent said initiator from being activated, and wherein one or more neutralizers are present in said second portion to neutralize said one or more inhibitors and activate said initiator.

4. The method of claim 1, wherein said binding pair partner is an antibody.

5. The method of claim 1, wherein said solid support is a surface of a reaction slide in which the assay is performed.

6. The method of claim 1, wherein said solid support is said magnetic particles.

7. The method of claim 1, wherein said solid support is non-magnetic particles.

8. The method of claim 2, wherein said reaction cascade initiator is an enzyme in said reaction cascade.

9. The method of claim 1, wherein said optical means comprises a photodetector and a light-emitting source.

10. The method of claim 9, wherein said light-emitting source is a 900 nanometer light-emitting diode.

11. The method of claim 1, wherein said magnetic field is a rotating magnetic field.

12. The method of claim 1, wherein said magnetic field is an oscillating magnetic field.

13. The method of claim 1, wherein said magnetic field is a moving static magnetic field.

14. The method of claim 1, wherein said coagulation cascade is selected from the group consisting of human blood coagulation cascade, bovine blood coagulation cascade, porcine blood coagulation cascade, bovine milk coagulation cascade, horseshoe crab hemolymph cascade, and insect blood coagulation cascade.

15. The method of claim 1, wherein said one or more cascade components are provided as a pooled plasma sample.

16. The method of claim 1, wherein said reaction cascade is a mammalian blood coagulation cascade.

17. The method of claim 1, wherein said binding pair partner is a receptor molecule.

18. The method of claim 17, wherein said steric mechanism is employed.

19. The method of claim 17, wherein said exclusion mechanism is employed.

20. The method of claim 1, wherein said binding pair partner is a ligand.

21. The method of claim 1, wherein said dry reagent contains a Factor IXa conjugate.

22. The method of claim 1, wherein the analyte is a low molecular weight molecule of <2000 Daltons.

23. The method of claim 1, wherein the analyte is an antiarrhythmic drug.

24. The method of claim 1, wherein the analyte is a hapten.

25. The method of claim 1, wherein the analyte is a peptide.

26. The method of claim 1, wherein the binding pair partner is an antibody and the analyte is a cell surface antigen.

27. The method of claim 1, wherein the binding pair partner is an antibody or antigen and the analyte is an antigen or antibody, respectively.

28. The method of claim 1, wherein said dry reagent contains a thrombin conjugate.

29. The method of claim 1, wherein said dry reagent contains a Factor Xa conjugate.

30. The method of claim 1, wherein said dry reagent contains a Factor IXa conjugate.

31. The method of claim 1, wherein said dry reagent contains a Russell's viper venom conjugate.

32. The method of claim 1, further comprising diluting said sample prior to said step of contacting the sample with the dry reagent.

33. A method for performing an affinity assay comprising:

a) contacting a sample to be assayed for the presence of an analyte with a dry reagent comprising:

1) a partner-conjugated initiator comprising a binding pair partner, which specifically binds with said analyte, conjugated to a reaction cascade initiator, wherein said reaction cascade initiator is an initiator for a reaction cascade selected from the group consisting of a lytic cascade and a coagulation cascade; and 2) magnetic particles, to form an assay mixture comprising (i) said partner-conjugated initiator bound to said analyte, and (ii) unbound partner-conjugated initiator, wherein a steric mechanism is selected to couple a binding pair interaction in said assay mixture with said reaction cascade, wherein:

in said steric mechanism, when said partner-conjugated initiator binds with said analyte, the reaction cascade initiator is sterically blocked from initiating the reaction cascade, providing a rate for the reaction cascade which is directly proportional to the amount of unbound partner-conjugated initiator, and thus inversely proportional to amount of said analyte in the sample;

b) incubating said assay mixture with one or more cascade components, to form an incubation mixture, wherein said one or more cascade components is present in an amount sufficient to make initial reaction of said initiator a rate-limiting step in said reaction cascade, wherein said one or more cascade components are sufficient to complete said reaction cascade upon initiation by said initiator, and wherein said one or more cascade components are either present in said dry reagent prior to said contacting step or added to said assay mixture after said contacting step;

c) applying a magnetic field to said assay mixture, wherein said magnetic field is an alternating magnetic field selected from the group consisting of an oscillating magnetic field, a rotating magnetic field and a moving static magnetic field;

d) activating said reaction cascade initiator to initiate said reaction cascade, wherein when said reaction cascade is a coagulation cascade, the coagulation cascade proceeds to formation of a fibrin clot and wherein when said reaction cascade is a lytic cascade, the lytic cascade proceeds by lysis of a fibrin clot;

e) monitoring a response of said magnetic particles to the magnetic field by an optical means to provide a time varying optical signal; and f) determining a concentration of said analyte in said sample by analysis of said time varying optical signal.

34. A kit, for performing an affinity assay, comprising:
a reaction slide having a reaction chamber;
a dry reagent contained in said reaction chamber, comprising an analyte to be assayed conjugated to a reaction cascade initiator, a binding pair partner that specifically binds with said analyte, and magnetic particles; wherein said reaction cascade initiator is an initiator for a reaction cascade selected from the group consisting of a lytic cascade and a coagulation cascade;
an amount of one or more additional cascade components effective to complete said reaction cascade upon initiation;
magnetic field generating means and optical means; and
means for amplifying and processing of a signal from said optical means to determine concentration of an analyte in a sample, wherein said signal represents a response of magnetic particles in a magnetic field generated by said magnetic field generating means.

35. The kit of claim 34, where said binding pair partner is an antibody or antigen.

36. The kit of claim 34, where said binding pair partner is a receptor or ligand.

37. The kit of claim 34, wherein said optical means comprises an illuminating source in the near infrared and a detection means.

38. The kit of claim 37, wherein said initiator is a light activated initiator and wherein said optical means further comprises an ultraviolet light source for activation of the initiator.

39. A method for performing an affinity assay comprising:
a) contacting a sample to be assayed for the presence of an analyte having more than 1 binding region with a first dry reagent to form an assay mixture in a first reaction chamber, said first dry reagent comprising:
1) a first binding pair partner immobilized on a solid support, wherein said first binding pair partner specifically binds with a first binding region of said analyte, and
2) a second binding pair partner that specifically binds with a second binding region of said analyte, wherein said second binding pair partner is conjugated to a reaction cascade initiator, wherein said reaction cascade initiator is an initiator for a reaction cascade selected from the group consisting of a lytic cascade and a coagulation cascade;

b) incubating said assay mixture to form (a) immobilized complexes of first binding pair partner/analyte/conjugated second binding pair partner and (b) free conjugated second binding pair partner;

c) transferring said free conjugated second binding pair partner to a second reaction chamber that contains a second dry reagent comprising magnetic particles and an effective amount of one or more additional cascade components to complete said reaction cascade upon initiation;

d) activating said reaction cascade initiator to initiate said reaction cascade, wherein when said reaction cascade is a coagulation cascade, the coagulation cascade proceeds to formation of a fibrin clot and wherein when said reaction cascade is a lytic cascade, the lytic cascade proceeds by lysis of a fibrin clot;

e) monitoring a response of said magnetic particles to an applied alternating magnetic field selected from the group consisting of an oscillating magnetic field, a rotating magnetic field and a moving static magnetic field by optical means to provide a time varying optical signal; and f) determining a concentration of said analyte in said sample by analysis of said time varying optical signal.

40. The method of claim 39, wherein said analyte is Apolipoprotein B, said first binding pair partner is a polyclonal antibody specific for a first epitope of Apolipoprotein B, said initiator is thrombin, said second antibody bound to said initiator is a monoclonal antibody having specificity for a second epitope of Apolipoprotein B, said solid support is magnetic particles, and said additional cascade component is fibrinogen, wherein:
said second dry reagent further comprises a buffer and wherein said solid support of said first dry reagent is retained in said first reaction chamber by application of a magnetic field just prior to transfer of said free conjugated second binding pair partner to said second reaction chamber.

41. The method of claim 39, wherein said analyte is CKMB, said first binding pair partner is an antibody specific for a "B" region epitope of CKMB, said solid support is magnetic particles, said initiator is Russell's viper venom, and said second binding pair partner is an antibody specific for a "M" region epitope of CKMB, wherein;
said one or more additional cascade components of said second dry reagent are Clotting Factor X, Factor V, phospholipid, prothrombin, calcium and fibrinogen, and wherein said second dry reagent further comprises a buffer; wherein said solid support of said first dry reagent is retained in said first reaction chamber by application of a magnetic field just prior to transfer of said free conjugated second binding pair partner to said second reaction chamber.

42. The method of claim 39, wherein said initiator activation step comprises illuminating said reaction cascade initiator with ultraviolet light.

43. The method of claim 39, wherein said one or more additional cascade components are provided as a pooled plasma sample.

44. The method of claim 39, wherein said analyte is an antigen, said first binding pair partner is a polyclonal antibody and said second pair partner is a monoclonal antibody.

45. The method of claim 39, wherein said dry reagent contains a Factor IXa conjugate.

46. The method of claim 39, wherein the analyte is selected from the group consisting of high molecular weight molecules of >2000 Daltons, cells, cell fragments and viruses.

47. The method of claim 39, wherein the analyte is an apolipoprotein.

48. The method of claim 39, wherein the analyte is a protein.

49. The method of claim 39, wherein the analyte is selected from the group consisting of lipoproteins, apolipoproteins, hormones, enzymes, external cell signal and structural elements, internal cell signal and structural elements and polynucleotides.

50. The method of claim 39, wherein said dry reagent contains a thrombin conjugate.

51. The method of claim 39, wherein said dry reagent contains a Russell's viper venom conjugate or a Factor IXa conjugate.

52. The method of claim 39, wherein said dry reagent contains a Factor Xa conjugate.

53. The method of claim 39, further comprising diluting the sample prior to said step of contacting the sample with the dry reagent.

54. A method for performing an affinity assay comprising:
   a) contacting a sample to be assayed for the presence of an analyte having more than 1 binding region with a dry reagent to form an assay mixture in a reaction chamber, said dry reagent comprising:
      1) a first binding pair partner immobilized on a solid support, wherein said first binding pair partner specifically binds with a first binding region of said analyte, and
      2) a second binding pair partner that specifically binds with a second binding region of said analyte, wherein said second binding pair partner is conjugated to a reaction cascade initiator, wherein said reaction cascade initiator is an initiator for a reaction cascade selected from the group consisting of a lytic cascade and a coagulation cascade and wherein said reaction cascade initiator is a triggerable initiator;
   b) incubating said assay mixture to form (a) immobilized complexes of first binding pair partner/analyte/conjugated second binding pair partner and (b) free conjugated second binding pair partner;
   c) washing said free conjugated second binding pair partner out of said reaction chamber with a wash solution to provide said immobilized complexes of first binding pair partner/analyte/conjugated binding pair partner, magnetic particles and said wash solution remaining in said reaction chamber;
   d) providing to said reaction chamber an effective amount of one or more cascade components to complete said reaction cascade upon initiation;
   e) triggering said reaction cascade initiator to initiate said reaction cascade, wherein when said reaction cascade is a coagulation cascade, the coagulation cascade proceeds to formation of a fibrin clot and wherein when said reaction cascade is a lytic cascade, the lytic cascade proceeds by lysis of a fibrin clot;
   f) monitoring a response of said magnetic particles to an applied alternating magnetic field selected from the group consisting of an oscillating magnetic field, a rotating magnetic field and a moving static magnetic field by optical means to provide a time varying optical signal; and
   g) determining a concentration of said analyte in said sample by analysis of said time varying optical signal.

55. The method of claim 54, wherein said triggering step comprises illuminating said reaction cascade initiator with ultraviolet light.

56. The method of claim 54, wherein said analyte is an antigen, said first binding pair partner is a polyclonal antibody and said second pair partner is a monoclonal antibody.

57. A kit, for performing an affinity assay, comprising:
   a reaction slide having two reaction chambers;
   a dry reagent contained in each of said reaction chambers, comprising a first dry reagent in a first reaction chamber, comprising a first binding pair partner immobilized on a solid support, wherein said first binding pair partner specifically binds with a first binding region of an analyte, and a second binding pair partner that specifically binds with a second binding region of said analyte, wherein said second binding pair partner is conjugated to a reaction cascade initiator, wherein said reaction cascade initiator is an initiator for a reaction cascade selected from the group consisting of a lytic cascade and a coagulation cascade,
   and a second dry reagent in a second reaction chamber comprising magnetic particles and an effective amount of one or more additional cascade components to complete a cascade reaction upon initiation; and
   magnetic field generating means and optical means.

58. The kit of claim 57, wherein said optical means comprises an illuminating source in the near infrared and a detection means.

59. The kit of claim 57, wherein said initiator is a light activated initiator and wherein said optical means further comprises an ultraviolet light source for activation of the initiator.

60. A diagnostic system for performing affinity assays comprising:
   a) a reaction slide comprising:
      1) a sample well for application of a sample to be analyzed;
      2) one or more reaction chambers connected to and in fluid communication with the sample well; and
      3) dry chemistry reagents and magnetic particles in each of the one or more reaction chambers, wherein the dry chemistry reagents comprise an analyte conjugated to a reaction cascade initiator, a binding pair partner which specifically binds to said analyte, and one or more coagulation cascade reagents;
   b) one or more means of generating a rotating magnetic field;
   c) one or more optical detection systems comprising illumination means and detection means; and
   d) one or more means for amplifying and processing of a signal from each of said optical detection systems to determine the concentration of one or more analytes in a sample, wherein said signal represents a response of magnetic particles in said rotating magnetic field.

61. The diagnostic system of claim 60, wherein said sample well of said reaction slide is in fluid communication with a parallel array of reaction chambers, each containing a different dry chemistry formulation; a plurality of said means for generation of rotating magnetic fields, with one for each separate reaction chamber; a plurality of optical detection systems, with one for each separate reaction chamber; and amplification and signal processing means for analysis of multiple analytes in the sample.

62. The diagnostic system of claim 60, also comprising means for delivery of ultraviolet light to said reaction chamber.

63. The diagnostic system of claim 60, wherein each of said one or more reaction chambers comprises: a first chamber for performing an affinity reaction, a second chamber adjacent to and in fluid communication with said first chamber for performing a coagulation cascade reaction, means for transferring liquid from said first chamber to said adjacent second chamber, and a rotating magnetic field for each chamber.

64. The diagnostic system of claim 61, comprising a parallel array of first chambers for performing affinity reactions, means for transferring liquid from each of the first chambers to a second chamber adjacent to each of said first chambers and in fluid communication therewith for performing a coagulation cascade reaction, magnetic particles in each chamber, and a rotating magnetic field for each chamber, allowing for analysis of multiple analytes in the sample.

65. The diagnostic system of claim 64, wherein said parallel array of reaction chambers contain, individually, a dry reagent formulation for analysis of Apo B-100, Apo A-1 and Apo(a), respectively, for assessment of atherosclerosis risk.

66. The diagnostic system of claim 64, wherein said parallel array of reaction chambers contain, individually, a dry reagent formulation for analysis of CKMB, troponin T, myoglobin, fibrinopeptide A, and fibrinogen, respectively for confirmation of acute myocardial infarction.

67. The diagnostic system of claim 60, further comprising a heating means for temperature control and a means for identification of reaction slide and sample.

68. The diagnostic system of claim 60, further comprising a vent in said reaction chamber, wherein said vent is covered by a hydrophobic membrane, and a means for applying a vacuum to said vent to provide a motive force for moving the sample from said sample well to said reaction chamber.

69. The diagnostic system of claim 60, further comprising an inlet in said sample well, a vent in said reaction chamber, wherein said vent is covered by a hydrophobic membrane, and a means for applying pressure to said inlet to provide a motive force for moving the sample from said sample well to said reaction chamber.

70. The diagnostic system of claim 60, further comprising an inlet in said sample well with a luer adapter affixed thereto, a vent in said reaction chamber, wherein said vent is covered by a hydrophobic membrane, and a syringe means docked to said luer adapter for applying pressure to a liquid sample to provide motive force for moving the sample into said sample well and into said reaction chamber.

71. A diagnostic system for performing affinity assays comprising:
   a) a reaction panel test card comprising:
      1) a sample well for application of a sample to be analyzed;
      2) a plurality of reaction chambers connected to and in fluid communication with the sample well; and
      3) one or more dry chemistry reagent mixtures and magnetic particles, in each of the reaction chambers, wherein at least one of said one or more dry chemistry reagent mixtures must comprise either (i) an analyte conjugated to a reaction cascade initiator, a binding pair partner which specifically binds to said analyte, and magnetic particles, or (ii) a binding pair partner which specifically binds with said analyte and is conjugated to a reaction cascade initiator, such that binding of said analyte to said binding pair partner sterically interferes with initiator molecule function, and magnetic particles; and
         wherein at least one of said one or more dry chemistry reagent mixtures must comprise a coagulation cascade reagent;
   b) one or more means of generating a rotating magnetic field;
   c) one or more optical detection systems comprising illumination means and detection means; and
   d) means for amplifying and processing of signals from said optical detection systems to determine the concentrations of analytes in a sample, wherein said signals represent responses of magnetic particles in said one or more rotating magnetic fields.

72. The system of claim 71, wherein each dry chemistry reagent contained in each of said plurality of reaction chambers has been subjected to preparation conditions which differ from the preparation conditions of the other dry chemistry reagents contained in the rest of said plurality of reaction chambers prior to placement on the panel test card and connection to said sample well.

73. A method for performing an affinity assay comprising:
   a) contacting a sample to be assayed for the presence of an analyte with a dry reagent comprising:
      1) an analyte-conjugated zymogen comprising said analyte conjugated to a zymogen of a reaction cascade, wherein said reaction cascade is selected from the group consisting of a lytic cascade and a coagulation cascade;
      2) a binding pair partner which specifically binds to said analyte;
      3) a reaction cascade initiator, wherein said reaction cascade initiator is an initiator for said reaction cascade and is any enzyme from said reaction cascade that is higher in said reaction cascade than said zymogen; and
      4) magnetic particles,
   to form an assay mixture in a reaction chamber comprising (i) said binding pair partner bound to said analyte, (ii) said binding pair partner bound to said analyte-conjugated zymogen, (iii) unbound analyte-conjugated zymogen and (iv) said reaction cascade initiator, wherein either a steric or exclusion mechanism is selected to couple a binding pair interaction in said assay mixture with said reaction cascade, wherein:
      in said steric mechanism, when the binding pair partner binds with the analyte-conjugated zymogen, the zymogen is sterically blocked from participating in the reaction cascade, such that upon activation of said reaction cascade initiator, the reaction cascade proceeds at a rate which is directly proportional to the amount of said unbound analyte-conjugated zymogen, and thus directly proportional to amount of said analyte in the sample, and
      in said exclusion mechanism, the binding pair partner that specifically binds with said analyte is bound to a solid support and any analyte present in said sample will compete with said analyte-conjugated zymogen for reaction with said binding pair partner, wherein initiation of the reaction cascade by activation of said reaction cascade initiator provides a rate of the reaction cascade which is directly proportional to the amount of said unbound analyte-conjugated zymogen and thus directly proportional to the amount of said analyte in the sample;
   b) separating the solid support including (i) said binding pair partner bound to said analyte and (ii) said binding pair partner bound to said analyte-conjugated zymogen from (iii) said unbound analyte-conjugated zymogen and said reaction cascade initiator, when said exclusion mechanism is employed;
   c) incubating either (i) said assay mixture when said steric mechanism is employed or (ii) said unbound analyte-conjugated zymogen and reaction cascade initiator when said exclusion mechanism is employed, with one or more cascade components to form an incubation mixture, wherein said one or more cascade components is present in an amount sufficient to make initial reaction of said zymogen activated by said reaction cascade initiator a rate limiting step in said reaction cascade and wherein said one or more cascade components are sufficient to complete said reaction cascade upon initiation, and wherein when said exclusion mechanism is employed, said one or more cascade components are added to said assay mixture after said contacting step, or when said steric mechanism is employed, said one or more cascade components are either present in said dry reagent prior to said contacting step or added to said assay mixture after said contacting step;

d) applying a magnetic field to said assay mixture, wherein said magnetic field is an alternating magnetic field selected from the group consisting of an oscillating magnetic field, a rotating magnetic field and a moving static magnetic field;

e) activating said reaction cascade initiator to initiate said reaction cascade, wherein when said reaction cascade is a coagulation cascade, the coagulation cascade proceeds to formation of a fibrin clot, and wherein when said reaction cascade is a lytic cascade, the lytic cascade proceeds by lysis of a fibrin clot;

f) monitoring a response of said magnetic particles to the magnetic field by an optical means to provide a time varying optical signal; and g) determining a concentration of said analyte in said sample by analysis of said time varying optical signal.

74. The method of claim 73 wherein said reaction cascade initiator is a triggerable enzyme that is higher in the reaction cascade than said zymogen bound to said analyte.

75. The method of claim 73, wherein said reaction cascade initiator is activated by exposure to light or heat.

76. The method of claim 73, wherein said binding pair partner is an antibody.

77. The method of claim 76, wherein said steric mechanism is employed.

78. The method of claim 76, wherein said exclusion mechanism is employed.

79. The method of claim 73, wherein said optical means comprises a photodetector and a light-emitting source.

80. The method of claim 79, wherein said light-emitting source is a 900 nanometer light-emitting diode.

81. The method of claim 73, wherein said magnetic field is a rotating magnetic field.

82. The method of claim 73, wherein said magnetic field is an oscillating magnetic field.

83. The method of claim 73, wherein said magnetic field is a moving static magnetic field.

84. The method of claim 73, wherein said coagulation cascade is selected from the group consisting of human blood coagulation cascade, bovine blood coagulation cascade, porcine blood coagulation cascade, bovine milk coagulation cascade, horseshoe crab hemolymph cascade, and insect blood coagulation cascade.

85. The method of claim 73, further comprising diluting the sample prior to said step of contacting the sample with the dry reagent.

86. A method for performing an affinity assay comprising:

a) contacting a sample to be assayed for the presence of an analyte with a dry reagent comprising:

1) a partner-conjugated initiator comprising a binding pair partner that specifically binds with said analyte and is conjugated to a reaction cascade initiator, wherein said reaction cascade initiator is an initiator for a reaction cascade selected from the group consisting of a lytic cascade and a coagulation cascade; and 2) magnetic particles;

to form an assay mixture in a reaction chamber, comprising (i) unbound partner-conjugated initiator, and (ii) said partner-conjugated initiator bound to said analyte, wherein a steric mechanism is selected to couple a binding pair interaction in said assay mixture with said reaction cascade, such that when the partner-conjugated initiator binds to said analyte, the reaction cascade initiator is sterically blocked from initiating the reaction cascade, providing a rate for the reaction cascade which is directly proportional to the amount of said unbound partner-conjugated initiator and thus inversely proportional to amount of said analyte in the sample;

b) incubating said assay mixture with one or more cascade components to form an incubation mixture, wherein said one or more cascade components is present in an amount sufficient to make initial reaction of said initiator a rate-limiting step in said reaction cascade, wherein said one or more cascade components are sufficient to complete said reaction cascade upon initiation by said initiator, and wherein said one or more cascade components are either present in said dry reagent prior to said contacting step or added to said assay mixture after said contacting step;

c) applying a magnetic field to said assay mixture, wherein said magnetic field is an alternating magnetic field selected from the group consisting of an oscillating magnetic field, a rotating magnetic field and a moving static magnetic field;

d) activating said reaction cascade initiator to initiate said reaction cascade, wherein when said reaction cascade is a coagulation cascade, the coagulation cascade proceeds to formation of a fibrin clot and wherein when said reaction cascade is a lytic cascade, the lytic cascade proceeds by lysis of a fibrin clot;

e) monitoring a response of said magnetic particles to the magnetic field by an optical means to provide a time varying optical signal; and f) determining a concentration of said analyte in said sample by analysis of said time varying optical signal.

* * * * *